(12) United States Patent
Wang et al.

(10) Patent No.: US 8,722,056 B2
(45) Date of Patent: May 13, 2014

(54) METHODS FOR MAKING AND COMPOSITIONS COMPRISING FERMENTATION PRODUCTS OF CORDYCEPS SINENSIS

(75) Inventors: Ya-Chun Wang, Yanshui Township, Tainan County (TW); Wang-Sheng Ko, Taichung (TW); Chih-Cheng Chang, Shoufeng Township, Hualien County (TW)

(73) Assignee: TCM Biotech International Corp., Taipei (TW)

( * ) Notice: Subject to any disclaimer, the term of this patent is extended or adjusted under 35 U.S.C. 154(b) by 865 days.

(21) Appl. No.: 12/461,304

(22) Filed: Aug. 6, 2009

(65) Prior Publication Data

US 2010/0021426 A1    Jan. 28, 2010

Related U.S. Application Data

(60) Continuation-in-part of application No. 12/411,940, filed on Mar. 26, 2009, now abandoned, which is a continuation of application No. 12/003,736, filed on Dec. 31, 2007, now abandoned, which is a division of application No. 10/755,468, filed on Jan. 13, 2004, now abandoned.

(30) Foreign Application Priority Data

Oct. 3, 2003  (TW) ................ 92127864 A

(51) Int. Cl.
*A61K 36/06* (2006.01)
(52) U.S. Cl.
USPC ....................... 424/195.15; 424/115
(58) Field of Classification Search
None
See application file for complete search history.

(56) References Cited

U.S. PATENT DOCUMENTS

| | | | |
|---|---|---|---|
| 6,126,942 | A | 10/2000 | Yang |
| 6,271,003 | B1 | 8/2001 | Hseu et al. |
| 6,737,065 | B2 | 5/2004 | Song et al. |
| 6,921,634 | B2 | 7/2005 | Lemon et al. |
| 2003/0095982 | A1 | 5/2003 | Lin |
| 2004/0137080 | A1* | 7/2004 | Cremisi ............... 424/702 |
| 2006/0094689 | A1 | 5/2006 | Kristiansen et al. |
| 2007/0004022 | A1 | 1/2007 | Shen |
| 2008/0299645 | A1 | 12/2008 | Cleaver et al. |

FOREIGN PATENT DOCUMENTS

| | | | |
|---|---|---|---|
| CN | 1168285 A | * | 12/1997 |
| CN | ZL99106135.7 | | 5/2003 |
| CN | ZL200310101281.1 | | 9/2006 |
| TW | 192356 | | 12/2003 |
| TW | 258373 | | 7/2006 |
| WO | PCT/CN98/00258 | | 5/1999 |
| WO | WO9921961 A1 | * | 5/1999 |

OTHER PUBLICATIONS

Batey R. et al., "Double blind placebo controlled prospective trial to investigate the effect of *Cordyceps sinensis* supplementation in minimizing anxiety, depression and fatigue associated with chronic hepatitis C," Abstract of Poster Presentation at the 6th International Mainlanders Hepatitis C Conference in Lisbon, Portugal, Feb. 7-8, 2002.
Buenz E.J. et al., "The traditional Chinese medicine *Cordyceps sinensis* and its effects on apoptotic homeostasis," Journal of Ethnopharmacology, 96:19-29 (2005).
Chen Y. et al., "Determination of the anamorph of *Cordyceps sinensis* inferred from the analysis of the ribosomal DNA internal transcribed spacers and 5.8 rDNA," Biochemical Systematics and Ecology, 29(6):597-607 (2001).
Cohen M. R. et al., The Hepatitis C Help Book, Chapter 7: Western Medication for Treatment of Hepatitis C, Chapter 8: Chinese Herbal Therapy for Hepatitis C, St. Martin's Press, New York (2000).
Gong H. et al., "Effects of *Cordyceps sinensis* on T lymphocyte subsets and hepatofibrosis in patients with chronic hepatitis B," Hunan Yi Ke Da Xue Xue Bao, 25(3):248-50 (2000).
Huang B. et al., "Upregulation of steroidogenic enzymes and ovarian 17β-estradiol in human granulosa-lutein cells by *Cordyceps sinensis* mycelium," Biology of Reproduction, 70:1358-64 (2004).
Jin D. et al., "Mycelial extract of *Cordyceps ophioglossoides* prevents neuronal cell death and ameliorates β-amyloid peptide-induced memory deficits in rats," Biol. Pharm. Bull., 27(7):1126-29 (2004).
Kim G. et al., "Water extract of *Cordyceps militatis* enhances maturation of murine bone marrow-derived dendritic cells in vitro," Biol. Pharm. Bull, 29(2):354-60 (2006).
Ko W., "Supplement therapeutic effect of compound *Cordyceps* preparation in treatment of liver damage," Dissertation Abstract No. 095HKU05111007 (1995).
Koh J. et al., "Activation of macrophages and the intestinal immune system by an orally administered decoction from cultured mycelia of *Cordyceps sinensis*," Biosci. Biotechnol. Biochem., 66(2):407-11 (2002).
DW 1995-348306, Sep. 12, 1995, JPX.
DW-1997-333538, Aug. 16, 1995, JPX.
Koh J. et al., "Antifatigue and antistress effect of hot-water fraction from mycelia of *Cordyceps sinensis*," Biol. Pharm. Bull., 26(5):691-94 (2003).
Kuo C. et al., "*Cordyceps sinensis* mycelium protects mice from group A streptococcal infection," Journal of Medical Microbiology, 54:795-802 (2005).
Marino E. et al., "Pharmacist intervention in treatment of patients with genotype 1 chronic hepatitis C," Journal of Managed Care Pharmacy, 15(2):147-50 (2009).

(Continued)

*Primary Examiner* — Chris R Tate
*Assistant Examiner* — Randall Winston
(74) *Attorney, Agent, or Firm* — Finnegan, Henderson, Farabow, Garrett & Dunner LLP.

(57) ABSTRACT

The present invention relates to novel and non-obvious methods and media for preparing fermentation products of *Cordyceps sinensis*. The present invention also relates to novel and non-obvious compositions comprising fermentation products of *Cordyceps sinensis* produced by the methods of the invention or obtained from other sources. The present invention also relates to novel and non-obvious methods of treating patients by administering the compositions of the invention. In one embodiment, the *Cordyceps sinensis* mycelia is *Paecilomyces hepiali* mycelia. In another embodiment the compositions of the invention are used to treat patients infected with hepatitis C.

21 Claims, 2 Drawing Sheets

(56) References Cited

OTHER PUBLICATIONS

Mukai M. et al., "Blockade of the aryl hydrocarbon receptor pathway triggered by dixin, polycyclb aromatic hydrocarbons and cigarette smoke by *Phellinus linteus*," Biol. Pharm. Bull., 31(10):1888-93 (2008).

Oh J. et al., "Apoptosis of human hepatocarcinoma (HepG2) and Neuroblastoma (SK-N-SH) cells induced by polysaccharides-peptide complexes produced by submerged mycelia culture of an entomopathogenic fungus *Cordyceps sphecocephala*," J. Microbiol. Biotechnol., 18(3):512-19 (2008).

Russell R. et al., "*Cordyceps*—A traditional Chinese medicine and another fungal therapeutic biofactory?," Phytochemistry, 69:1469-95 (2009).

Sung G. et al., "Phylogenetic classification of *Cordyceps* and the clavicipitaceous fungi," Studies in Mycology, 57:5-59 (2007).

Tan S.L., Hepatitis C Viruses: Genomes and Molecular Biology, Chapter 1: HCV Genome and Life Cycle by Stéphane Chevaliez and Jean-Michel Pawlotsky, Horizon Bioscience, United Kingdom (2006).

"TCM Biotech International Corp., Unlocking the power of traditional Chinese Medicine," Nature Jobs, 5:13 (2007).

Yu M. et al., "Rapid virological response and treatment duration for chronic hepatitis C genotype 1 patients: A randomized trial," Hepatology, 47:1884-93 (2008).

Zhang Q. et al., "*Cordyceps sinensis* mycelium extract induces human premyelocytic leukemia cell apoptosis through mitochondrion pathway," Exp. Biol. Med., 232:52-57 (2007).

Zhou X. et al., "*Cordyceps* fungi: natural products, pharmacological functions and developmental products," Journal of Pharmacy and Pharmacology, 61:279-91 (2009).

Zhu J. et al., "The scientific rediscovery of an ancient Chinese herbal medicine: *Cordyceps sinensis* part I," Journal of Alternative and Complementary Medicine, 4(3):289-303 (1998).

Zhu J. et al., "The scientific rediscovery of a precious ancient Chinese herbal regimen: *Cordyceps sinensis* part II," Journal of Alternative and Complementary Medicine, 4(4):429-57 (1998).

Dong et al., "Nutritional requirements of mycelial growth of *Cordyceps sinensis* in submerged culture," *Journal of Applied Microbiology*, 99: 483-492 (2005).

E-mail communication dated Jul. 31, 2012, from Gourmet Mushrooms, Inc.

"CordyMax® Healthcare Professional Product Guide—A Scientific Product Review" pp. 1-8 (2000).

"Jinshuibac Tablets and Capsules" *Pharmacopoeia of the People's Republic of China* vol. 1, pp. 495-497 (2005).

"Optimization of *Paecilomyces Hepial's* Fermentation Medium by One-factor-at-a-time Experiments" 7 pages.

Chen, "Progress in Traditional Chinese Medicine" *Trends Pharmacol. Sci.* 16(6):182-87 (1995).

Dai et al., "CordyMax™ Cs-4 Improves Steady-State Bioenergy Status in Mouse Liver" *J. Altera. Complement Med.* 7(3):231-40 (2001).

Dai et al., "CordyMax™ Cs-4 Improves Steady-State energy Status in Mouse Liver".

Dong et al., "Nutritional Requirements of Mycelial Growth of *Cordyceps Sinensis* in Submerged Culture" *J. Appl, Microbiol.* 99(3):483-92 (2005).

Feld et al,, "Mechanism of Action of Interferon and Ribavirin in Treatment of Hepatitis C" *Nature* 436(7053):967-72 (2005).

Rehermann et al., "Immunology of Hepatitis B Virus and Hepatitis C Virus Infection" *Nat. Rev. Immunol.* 5(3):215-29 (2005).

Wang et al., "A Computational Approach to Botanical Drug Design by Modeling Quantitative Composition—activity Relationship" *Chem. Biol. Drug Des.* 68(3):166-72 (2006).

Xue et al., "Studying Traditional Chinese Medicine" *Science* 300(5620):740-41 (2003).

\* cited by examiner

METHODS FOR MAKING AND COMPOSITIONS COMPRISING FERMENTATION PRODUCTS OF CORDYCEPS SINENSIS

RELATED APPLICATIONS

This application is a continuation-in-part of U.S. patent application Ser. No. 12/411,940, filed Mar. 26, 2009 now abandoned, which is a continuation of U.S. patent application Ser. No. 12/003,736, filed Dec. 31, 2007 now abandoned, which is a division of U.S. patent application Ser. No. 10/755,468, filed Jan. 13, 2004 now abandoned, which claims priority under 35 U.S.C. §119(a) to Taiwan Patent Application No. 092127864, filed Oct. 3, 2003, all of which are incorporated herein by reference.

FIELD OF THE INVENTION

The present invention relates to novel and non-obvious methods and media for preparing fermentation products of *Cordyceps sinensis*. The present invention also relates to novel and non-obvious compositions comprising fermentation products of *Cordyceps sinensis* produced by the methods of the invention or obtained from other sources. The present invention also relates to novel and non-obvious methods of treating patients by administering the compositions of the invention. In one embodiment, the *Cordyceps sinensis* mycelia is *Paecilomyces hepiali* mycelia. In another embodiment the compositions of the invention are used to treat patients infected with hepatitis C.

BACKGROUND OF THE INVENTION

A. *Cordyceps sinensis*

*Cordyceps sinensis* (Berk.) Sacc., also known as Chinese caterpillar fungus and "DongChongXiaCao," is a black, blade-shaped fungus found primarily at high altitudes in the mountains of northwest and southwest China. The fungus is parasitic, growing on and deriving nutrients from the larvae of moths in the genera *Hepialus* and *Thitarodes*. *Cordyceps sinensis* spores infect *Hepialus* and *Thitarodes* caterpillars in late summer or early fall while the caterpillars are hibernating underground. The fungus then multiplies by yeast-like budding and grows in the form of threadlike hyphae, ultimately killing the host. During the following spring, the fruiting body (i.e., the sexual, teleomorphic form) of the fungus grows out of the caterpillar's head and emerges above ground.

Because wild *Cordyceps sinensis* is rare, scientists have attempted to adapt anamorphic (asexual) forms of the fungus for growth under laboratory conditions. However, the isolated fungus is difficult to culture without a host due to its low growth rate and specialized nutritional requirements. In addition, it is difficult to obtain pure isolates from wild *Cordyceps sinensis* and as a result, the various laboratory cultures have not yielded uniform mycelia. Accordingly, the various isolates have been given different anamorph names, including: *Cephalosporium sinensis* (also called *Cephalosporium dongchongxiacao*), *Chrysosporium sinense*, *Hirsutella hepialid*, *Hirsutella sinensis*, *Mortierella hepiali*, *Paecilomyces hepiali*, *Paecilomyces sinensis*, *Scydalilum* sp., *Scytalidium hepiali*, *Sporothrix insectorum*, *Stachybotrys* sp., *Tolypocladimn sinensis*, etc. Recent molecular evidence has revealed that *Hirstuella sinensis* is the true anamorph of *Cordyceps sinensis*.

*Cordyceps sinensis* has a long history of medicinal use in China, and although the various isolates of *Cordyceps sinensis* are morphologically distinct, they share similar chemical compositions and pharmacological properties. A variety of bioactive ingredients have been isolated from *Cordyceps sinensis*, including: proteins, peptides, all essential amino acids, cyclic dipeptides, and polyamines; monosaccharides, polysaccharides, and sugar derivatives; cordycepin (3'deoxyadenosine); cordycepic acid (D-mannitol); sterols, including ergosterol; nucleosides and nucleotides; superoxide dismutase; fatty acids; metal elements; vitamins; and other inorganics.

*Cordyceps sinensis* has been reported to produce both immuno-stimulating and immunosuppressive effects. Thus, it appears that *Cordyceps sinensis* may be a bi-directional modulator of the immune system. For example, some studies reported that *Cordyceps sinensis* enhances the activities of macrophages and natural killer (NK) cells, while other studies reported that the fungus inhibits these activities under different circumstances. *Cordyceps sinensis* has been shown to suppress or enhance antibody production and the proliferation of T cells, thymocytes, and natural killer cells. *Cordyceps sinensis* has also been shown to suppress or enhance expression of IL1, IL2, IL6, IL10, CD4, CD5, CD8, CD25, tumor necrosis factor, interferons, etc. The combination of *Cordyceps sinensis* with persicae semen (peach seed) has been used to treat severe post-hepatitis cirrhosis by decreasing levels of IgG and IgA, increasing cell-lymphocyte rosette rate, enhancing the efficiency of natural killer cells, and increasing the $CD4^+/CD8^+$ cell ratio. In addition, *Cordyceps sinensis* has been shown to increase $CD4^+/CD8^+$ ratios and reduce the amount of viral proteins expressed in patients chronically infected with the hepadnavirus, hepatitis B.

In view of these potential therapeutic uses for *Cordyceps sinensis*, a need exists for a consistent and plentiful supply of highly bioactive material. Conventional cultivation methods for *Cordyceps sinensis* include solid media stationary incubation, liquid media rotating shaking incubation, liquid-state fermentation, and submerged liquid-state fermentation. However, current methods for producing *Cordyceps sinensis* fermentation products require substantial time and labor, and generally produce low yields of product with poor bioactivity.

For example, U.S. application Ser. No. 11/450,747 and International Application No. PCT/CN98/00258, which are incorporated herein by reference, disclose liquid culture methods for producing *Cordyceps sinensis* fermentation products. The method disclosed in the '747 application requires the following separate steps:
1. Isolating new fungal strains from nature;
2. Selecting fungal strains that are capable of developing stromata;
3. Plate-culturing on solid media for more than 10 generations, at least 5 generations of which are grown under low temperatures of 0-10° C.;
4. Performing a second cultivation in liquid culture media at a temperature of 12° C. on a rocking device for 12 days; and
5. Fermenting at a temperature of 12° C. in a starter vat for 10 days and then expanding the volume of culture media 10-fold until the needed quantity is reached.

The media used in the third step of the method disclosed in the '747 application contains beef tea, lactalbumin hydrolysate, yeast powder, glucose, milk, nucleic acid, magnesium sulfate, sodium dihydrogen phosphate, and vitamins. The media used in the fourth and fifth steps of the method disclosed in the '747 application contains silk worm chrysalis powder, protein peptone, corn flour, wheat gluten, glucose, magnesium sulfate, and dipotassium hydrogen phosphate.

The method disclosed in PCT/CN98/00258 also requires five separate culture steps involving:
1. Culturing a slant strain for 5-6 days;
2. Culturing a primary seed culture for 2-4 days;
3. Culturing a secondary seed culture for 2-4 days;
4. Culturing a scaled up seed culture for 3 days; and
5. Culturing a large scale fermentation culture for 5-6 days.

The media used in PCT/CN98/00258 contains glucose, sucrose, peptone, bran, $KH_2PO_4$, and $MgSO_4$.

From start to finish, large-scale fermentations according to these methods require long periods of time and generally do not yield highly bioactive product. The present invention improves upon these current large scale fermentation methods for manufacturing *Cordyceps sinensis* fungal mycelia, thereby satisfying longstanding needs in the art.

B. Hepatitis C Virus

Hepatitis C virus (HCV), also known as "non-A non-B hepatitis," is a contagious blood-borne virus. HCV is a member of the Flaviviridae family of viruses and comprises a single-stranded, positive-sense RNA genome that encodes a long polyprotein precursor of about 3,000 amino acids, which is processed by both cellular and viral proteases to yield at least 10 individual proteins. An estimated 150 to 200 million people worldwide are infected with hepatitis C, including nearly 4 million in the United States. The virus is cleared spontaneously in less than 20% of HCV-infected individuals, and in the majority of patients, the virus persists and causes chronic hepatitis that may lead to end-stage liver diseases, cancer, or even death.

Hepatitis C viruses have a high level of genetic heterogeneity and thus have been grouped by their degree of sequence identity into six separate genotypes (types 1 through 6), and further divided into numerous subtypes. Geographic distribution and responses to therapeutic treatments differ between genotypes. Genotypes 1a and 1b are the most prevalent in the United States and Western Europe, followed by genotypes 2 and 3. Among hepatitis C patients in northern Taiwan, approximately 58% to 73% are infected with genotype 1b and approximately 7.4% to 16.5% are infected with genotype 2a, while in southern Taiwan, around 48% to 64.3% are infected with genotype 1b and around 35% to 41% are infected with genotype 2a.

Hepatitis C therapy traditionally includes treatment with interferons, such as interferon-α 2A (ROFERON-A, Roche). Current hepatitis C therapy uses a combination of pegylated interferon-α, for example, PEGINTRON (Schering-Plough) or PEGASYS (Roche), and the guanosine analog, ribavirin, for example, REBETOL (Schering-Plough) or COPEGUS (Roche). The current standard therapy for treating chronic hepatitis C is a combination of weekly injections of pegylated interferon (IFN)-α 2A and daily oral doses of ribavirin for a period of 24 or 48 weeks. Both drugs are indirect antivirals because they do not target a specific HCV protein or genome element. A sustained viral response (SVR), which is defined as patients remaining HCV-free (undetectable levels of virus) for 6 months after the termination of therapy, is achieved in only half of the treated patients and in less than half of patients with high levels of virus. The SVR is higher in patients infected with genotypes 2 and 3, but much lower in patients infected with genotypes 1 and 4 through 6. In addition, the standard therapy is associated with considerable adverse effects, including: depression, fatigue, and "flu-like" symptoms such as fever, headache, muscle soreness, and nausea, caused by IFN-α; and hemolytic anemia, cough, rash, and insomnia, caused by ribavirin. These symptoms tend to disappear after two to three weeks, but then reappear, often with new side effects, at the end stage of therapy. Such late-stage adverse effects Include: severe fatigue and muscle soreness, leucopenia, anemia, dysphoria, weight loss, and hair loss.

Due to the side effects, the cost, and the inefficiency of the current standard therapy, there is a large unmet need for safe, effective HCV therapies. The instant invention solves some of the problems associated with current HCV therapy, thereby satisfying longstanding needs in the art.

SUMMARY OF THE INVENTION

The present invention relates to novel and non-obvious methods and media for preparing fermentation products of *Cordyceps sinensis*. The invention also relates to novel and non-obvious compositions comprising *Cordyceps sinensis* fermentation products and methods for treating various diseases or disorders by administering an effective amount of such compositions.

In one embodiment, the invention relates to a novel and non-obvious nutrient medium comprising:
about 1% to about 5% (w/w) of at least one carbon source;
about 0.1% to about 3% (w/w) of at least one nitrogen source;
about 0.05% to about 1% of at least one inorganic salt; and
about 0.01% to about 0.2% (w/w) manganese, and/or about 0.001% to about 0.01% (w/w) copper, and/or about 0.01% to about 0.2% (w/w) iron, and/or about 0.02% to about 0.2% cobalt, and/or about 0.05% to about 0.5% (w/w) calcium, and/or about 0.0003% to about 0.003% (w/w) selenium;
wherein the pH of the medium is about 5 to about 7.

In some embodiments the carbon source is about 1% to about 5% (w/w) sucrose and/or about 1% to about 5% (w/w) glucose. In other embodiments, the nitrogen source is about 0.2% to about 1.2% (w/w) yeast extract, and/or about 1.5% to about 3% (w/w) soy bean powder, and/or about 0.1% to about 0.35% (w/w) $(NH_4)_2HPO_4$. In other embodiments, the inorganic salt is about 0.1% to about 0.15% (w/w) $KH_2PO_4$, and/or about 0.5% to about 1% (w/w) $MgSO_4.7H_2O$, and/or about 0.1% to about 0.25% (w/w) $K_2HPO_4$, and/or about 0.05% to about 0.06% (w/w) KCl.

In another embodiment, the invention relates to a novel and non-obvious method for producing a *Cordyceps sinensis* fermentation product comprising:
a. inoculating a solid nutrient medium (i.e., a plate culture) with at least one strain of *Cordyceps sinensis* and incubating at about 18° C. to about 28° C. for about 4 to 8 days;
b. inoculating a flask comprising a first liquid nutrient medium (i.e., a seed culture) with at least a portion of the culture from (a) and incubating at about 18° C. to about 28° C. for about 2 to 4 days;
c. inoculating a second flask comprising liquid nutrient medium (i.e., a second, or scaled up seed culture) with at least a portion of the culture from (b) and incubating at about 18° C. to about 28° C. for about 2 to 3 days;
d. inoculating a vat chamber comprising liquid nutrient medium (i.e., a fermentation culture) with at least a portion of the culture from (c) and incubating at about 18° C. to about 28° C. for about 1 to 3 days; and
e. recovering the *Cordyceps sinensis* fermentation product.

In one embodiment, the *Cordyceps sinensis* is *Paecilomyces hepiali*.

In another embodiment, the invention relates to a novel and non-obvious method for producing a *Cordyceps sinensis* fermentation product comprising:
  a. inoculating a solid nutrient medium with at least one strain of *Cordyceps sinensis* and incubating at about 18° C. to about 28° C. for about 4 to 8 days;
  b. inoculating a flask comprising a first liquid nutrient medium (i.e., a seed culture) with at least a portion of the culture from (a) and incubating at about 18° C. to about 28° C. for about 2 to 4 days;
  c. inoculating a second flask comprising liquid nutrient medium (i.e., a second, or scaled up seed culture) with at least a portion of the culture from (b) and incubating at about 18° C. to about 28° C. for about 2 to 3 days;
  d. inoculating a vat chamber comprising liquid nutrient medium (i.e., a fermentation culture) with at least a portion of the culture from (c) and incubating at about 18° C. to about 28° C. for about 3 to 7 days; and
  e. recovering the *Cordyceps sinensis* fermentation product;
wherein the method does not comprise additional culture steps between steps (a) and (b), (b) and (c), and/or (c) and (d).

In one embodiment, the *Cordyceps sinensis* is *Hirsutella sinensis*.

The invention also relates to novel and non-obvious adjuvant compositions comprising a *Cordyceps sinensis* fermentation product. In some embodiments, the *Cordyceps sinensis* fermentation products used in the compositions of the invention are produced by the methods of the invention. In other embodiments, the *Cordyceps sinensis* fermentation products are obtained from other sources.

In some embodiments, the adjuvant compositions of the invention further comprise extracts from *Astragalus membranaceus*. In some embodiments, the adjuvant compositions of the invention further comprise zinc. In some embodiments, the adjuvant compositions comprise about 50% to about 90% (w/w) of a *Cordyceps sinensis* fermentation product, about 10% to about 50% (w/w) of *Astragalus membranaceus* extract, and/or about 5% to about 10% (w/w) zinc.

In some embodiments, the adjuvant compositions of the invention further comprise a conventional hepatitis C therapy. In some embodiments the conventional hepatitis C therapy comprises an interferon and a guanosine analog. In other embodiments, the interferon is interferon-α and the guanosine analog is ribavirin. In other embodiments, the interferon-α is pegylated.

The invention also relates to methods for treating patients infected with or who may have been exposed to hepatitis C comprising administering an effective amount of a composition comprising a conventional hepatitis C therapy and an adjuvant composition of the invention. In other embodiments, the invention relates to methods for treating patients infected with or who may have been exposed to hepatitis C comprising administering an effective amount of an adjuvant composition of the invention, and separately administering an effective amount of at least one conventional hepatitis C therapy. In some embodiments, the adjuvant compositions of the invention and conventional hepatitis C therapies are administered simultaneously. In other embodiments, the adjuvant compositions of the invention and conventional hepatitis C therapies are administered sequentially. In other embodiments, the adjuvant compositions of the invention and conventional hepatitis C therapies are administered spaced out over a period of time.

In some embodiments, the adjuvant compositions of the invention increase the effect and reduce the negative side effects of conventional hepatitis C therapies. In other embodiments, the adjuvant compositions of the invention increase the effect of conventional hepatitis C therapies by at least two-fold.

The invention also relates to methods for treating patients infected with or who may have been exposed to hepatitis B, comprising administering a therapeutically effective amount of an adjuvant composition of the invention.

DETAILED DESCRIPTION OF THE INVENTION

A. Definitions

Figure 1:
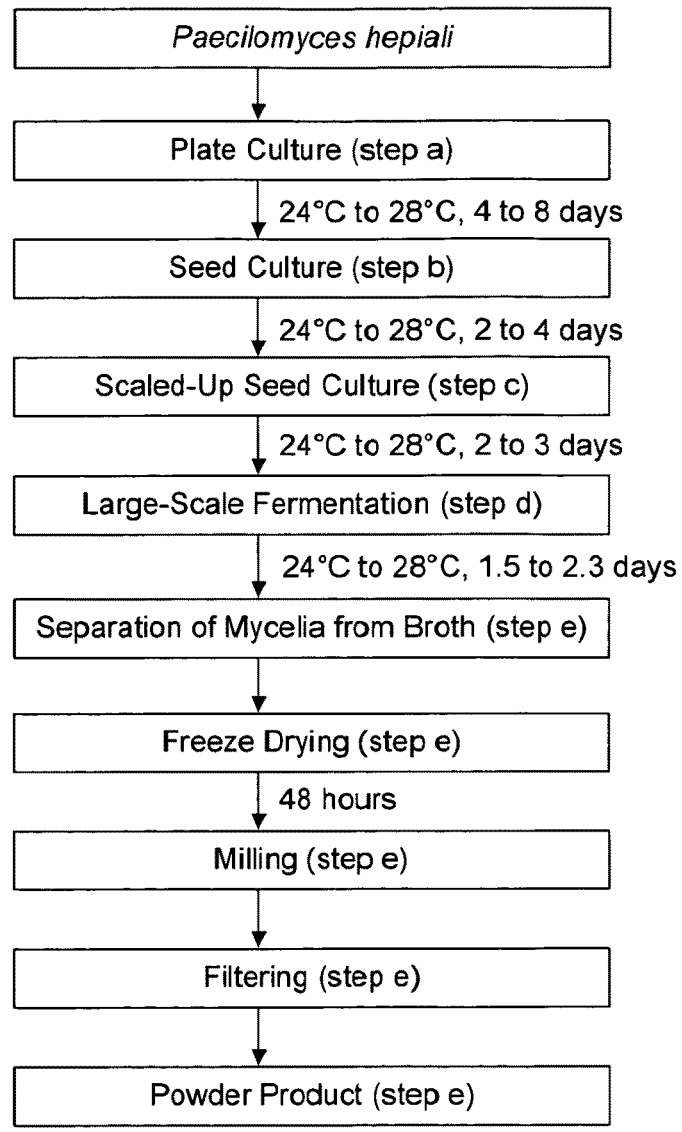
FIG. 1. Schematic representation of one embodiment of the method of the invention for *Paecilomyces hepiali* fermentation.

In the context of the present invention the following terms are to be understood as follows:

The term "*Cordyceps sinensis* fermentation product" as used herein refers to the product of a process of mycelial fermentation of one or more laboratory isolates of *Cordyceps sinensis*, including but not limited to: *Cephalosporium maydis*, *Cephalosporium sinensis* (also called *Cephalosporium dongchongxiacao*), *Chrysosporium sinense*, *Hirstuella hepialid*, *Hirsutella sinensis*, *Mortierella hepiali*, *Paecilomyces hepiali*, *Paecilomyces sinensis*, *Paecilomyces variotii*, *Scytalidium hepiali*, *Sporothrix insectorum*, *Stachybotrys chartarum*, *Stachybotrys clindrospora*, *Stachybotrys dichroa*, *Tolypocladium calcdonica*, *Tolypocladimn sinensis*, and *Verticillium bulbillosum*. The fermentation products of the invention are generally a light yellow to dark brown powder with a slightly bitter taste and aromatic odor.

The term "*Paecilomyces hepiali*" as used herein refers to the Chen et Dai strain of the *Cordyceps sinensis* fungus. Morphologically, when cultivated on potato dextrose agar (PDA) at 26° C. for about one month, the strain produces synnemata either singly or in clusters from the loose cottony aerial mycelia. The synnemata is white in color and turns to yellow upon aging. The aerial mycelia are yellow to orange in color. Under the microscope, the branching mycelia is transparent, septated, and about 2.5 to 4 μm in diameter. The conidiospores are arranged singly, alternately, or oppositely. Some flask-shaped conidiospores are arranged as a simple brush-like structure. The conidia on the conidiospores are near spherical in shape, smooth, and arranged in a single chain. In liquid culture grown under continuous agitation, the conidia may have a spherical or elliptical shape.

The term "*Astragalus membranaceus*" as used herein refers to the perennial leguminosae herbaceous plant also known as milk-vetch root. The plant is mainly cultivated in southern China, and the root has been used to prepare extracts for several therapeutic purposes. Numerous bioactive constituents of *Astragalus membranaceus* have been discovered, including polysaccharides, monosaccharides, flavonoids, alkaloids (such as choline and betaine), amino acids, glucuronic acid, folic acid, metallic elements (such as selenium), and diatomite materials.

The phrases "therapeutically effective amount" and "effective amount" as used herein mean an amount sufficient to provide a benefit in the treatment of a disease, or in the improvement of one's general health and sense of well-being. Therapeutically effective amounts will vary depending on the patient and symptoms being treated. In general, a therapeutically effective amount of *Cordyceps sinensis* fermentation product is about 0.1 g to about 30 g administered in single or divided daily doses. In some embodiments, the dose is about 1 g to about 10 g. In other embodiments, the dose is about 2 g to about 5 g. In other embodiments, the dose is 3.5, 3.6, 3.7, 3.8, 3.9, 4, 4.1, 4.2, 4.3, 4.4, or 4.5 g. In general, a therapeutically effective amount of *Astragalus membranaceus* extract is about 0.1 g to about 30 g administered in single or divided daily doses. In some embodiments, the dose is about 0.1 g to about 5 g. In other embodiments, the dose is about 3 g to about 7 g. In other embodiments, the dose is 1.0, 1.1, 1.2, 1.3, 1.4, or 1.5 g.

As used herein, the terms "mammal" and "patient" include, but are not limited to, domestic pets, farm animals and livestock, and humans.

As used herein, the terms "sustained viral response" and "SVR" are defined as patients remaining HCV-free (undetectable levels of virus) for 6 months after the termination of therapy.

As used herein, the term "interferon" includes recombinant and non-recombinant forms of interferon-$\alpha$, as well as pegylated and non-pegylated forms of interferon-$\alpha$.

As used herein, the term "conventional therapy" with respect to Hepatitis C refers to therapies comprising an interferon and a guanosine analog.

As used herein, the term "slant culture" refers to any culture made on the slanting surface of solid medium that has been solidified in a tube that has been inclined from the perpendicular in order to provide a greater surface area for growth.

As used herein, the term "seed culture" refers to any liquid culture incubated in a flask using a rocking device (shaker) before being transferred into a fermentor (vat) chamber.

As used herein, the term "fermentor culture" refers to any liquid culture incubated in a vat chamber used for growing large amounts of mycelia.

As used herein, the term "flask" refers to any container for holding a liquid of a volume at or below 2000 ml.

As used herein, the term "vat chamber" or "fementor chamber" refers to any container for holding a liquid of a volume at or greater than 10 L. Vat/fementor chambers often contain a temperature control system (such as a heater and/or cooler system) to provide a constant temperature, and an agitator for aeration.

As used herein, the term "about" with respect to any numerical value or range of values means±10%. All numerical values and ranges recited herein are to be understood as being modified by the term "about" even where not expressly stated.

B. Methods and Media for Producing *Cordyceps sinensis* Fermentation Products The invention provides novel and non-obvious methods and media for making *Cordyceps sinensis* fermentation products. The methods and media of the invention produce greater yields of *Cordyceps sinensis* fermentation products having improved potency in a time span much shorter than prior art methods. For example, the methods of the invention reduce the time required for fermentation by about 50% to about 90% compared to some prior art methods, and the resulting mycelia contain about 30% to about 80% more active ingredients than mycelia produced by some prior art methods. In addition, the methods and media of the invention eliminate the need for multiple seed cultures, substantially reducing the time and labor involved in producing *Cordyceps sinensis* mycelia compared to some prior art methods.

1. Nutrient Media

The novel and non-obvious nutrient media used in the methods of the invention may be solid and/or liquid. The media may comprise sources of carbon, nitrogen, inorganic salts, and trace elements. The media may further comprise any additional nutritional material that supports the growth, reproduction, fermentation catabolism, and anabolism of *Cordyceps sinensis* mycelia. The composition of the fermentation media of the invention may be varied depending on the strain of *Cordyceps sinensis* used.

Sources of carbon for the nutrient media of the invention may include carbohydrates such as sugars, for example, glucose, fructose, dextrose, maltose, mannitol, sucrose, xylose, and the like, and/or starches such as grains, for example, cornstarch, corn meal, oats, ryes, wheat germ, and the like. In general, the amount of carbohydrate usually varies from about 0.5% to about 10% by weight and often from about 1% to about 5%. The carbon sources may be used individually, or several carbon sources may be combined in the media. For example, in some embodiments, the media may contain about 1% to about 5% of sucrose and/or about 1% to about 5% of glucose. In other embodiments, the media may contain about 1.5% to about 2.5% of sucrose and/or about 1.5% to about 2.5% of glucose. In some embodiments, the media may contain 1.5%, 2%, 2.5%, 3%, 3.5%, or 4.5% of sucrose and/or 1.5%, 2%, 2.5%, 3%, 3.5%, or 4.5% of glucose.

Nitrogen sources for the nutrient media of the invention may include, for example, ammonium nitrate, ammonium sulfate, corn steep liquor, cottonseed flour, diammonium hydrogen phosphate, distiller's solubles, fish meal, hydrolysates of casein, meat extract, peanut meal, peptone, primary yeast, rice bran, sodium nitrate, soybean cake, soybean meal, soybean powder, tomato paste, yeast hydrolysates, and the like. In general, the amount of nitrogen source usually varies from about 0.05% to about 10% by weight and often from about 0.1% to about 5%. The nitrogen sources may be used individually, or several nitrogen sources may be combined in the media. For example, in some embodiments, the media contains about 0.1% to about 5% yeast powder and/or about 1% to about 5% soy bean powder and/or about 0.01% to about 0.5% diammonium hydrogen phosphate (($NH_4$)$_2$$HPO_4$). In other embodiments, the media contains about 0.2% to about 1.2% yeast powder and/or about 1.5% to about 3% soy bean powder and/or about 0.01% to about 0.035% ($NH_4$)$_2$$HPO_4$. In some embodiments, the media contains 0.35% yeast powder and/or other nitrogen sources. In other embodiments, the media contains 0.2%, 0.4%, 0.6%, 0.8%, 1.0%, or 1.2% yeast powder and/or 1.5%, 1.75%, 2.0%, 2.25%, 2.5%, 2.75%, or 3% soy bean powder and/or 0.01%, 0.015%, 0.02%, 0.025%, 0.03%, or 0.035% ($NH_4$)$_2$$HPO_4$, and/or other nitrogen sources.

Among the inorganic salts which may be used in the nutrient media of the invention are the customary salts capable of yielding ammonium, calcium, carbonate, chloride, magnesium, potassium, phosphate, sodium, sulfate, and like ions. Exemplary inorganic salts include $KH_2PO_4$, $MgSO_4 \cdot 7H_2O$, $K_2HPO_4$, and KCl. In general, the amount of inorganic salt usually varies from about 0.01% to about 1% % by weight and often from about 0.1% to about 0.5%. The inorganic salts may be used individually, or several inorganic salts may be combined in the media. For example, in some embodiments, the media contains about 0.01% to about 0.5% $KH_2PO_4$ and/or about 0.01% to about 1% $MgSO_4.7H_2O$ and/or about 0.02% to about 0.5% $K_2HPO_4$ and/or about 0.01% to about 0.5% KCl. In other embodiments, the media contains about 0.1% to about 0.15% $KH_2PO_4$ and/or about 0.05% to about 0.6% $MgSO_4.7H_2O$ and/or about 0.1% to about 0.25% $K_2HPO_4$ and/or about 0.05% to about 0.06% KCl. In other embodiments, the media contains 0.1%, 0.11%, 0.12%, 0.13%, 0.14%, or 0.15% $KH_2PO_4$ and/or 0.05%, 0.15%, 0.25%, 0.35%, 0.5%, 0.75%, or 1%, $MgSO_4.7H_2O$ and/or 0.1%, 0.13%, 0.2%, 0.23%, or 0.25% $K_2HPO_4$ and/or 0.05%, to 0.052%, 0.054%, 0.056%, 0.058%, or 0.060% KCl.

Among the trace elements which may be used in the nutrient media of the invention are barium, cadmium, calcium, chromium, cobalt, copper, iron, lead, manganese, molybdenum, nickel, selenium, strontium, zinc, etc. Sources of such trace elements may include, for example, $MnSO_4$, $CuSO_4.5H_2O$, $FeSO_4.7H_2O$, $CoSO_4.7H_2O$, $CaCl_2$, $KH_2PO_4$, $MgSO_4$, $Na_2SeO_3$, etc. In general, the amount of trace element usually varies from about 0.0001% to about 5% of the media and often from about 0.001% to about 0.5%. The trace elements may be used individually, or several trace elements may be combined in the media. For example, in some embodiments, the media contains about 0.01% to about 0.2% manganese and/or about 0.001% to about 0.01% copper and/or about 0.01% to about 0.2% iron and/or about 0.02% to about 0.2% cobalt and/or about 0.05% to about 0.5% calcium and/or about 0.0003% to about 0.003% selenium. In other embodiments, the media contains 0.02%, 0.03%, 0.04%, or 0.05% manganese (e.g., $MnSO_4$) and/or 0.001%, 0.002%, 0.003%, 0.004%, 0.005%, or 0.006% copper (e.g., $CuSO_4.5H_2O$) and/or 0.02%, 0.03%, 0.04%, 0.05%, 0.06%, 0.07%, 0.08%, 0.09%, or 0.1% iron (e.g., $FeSO_4.7H_2O$) and/or 0.02%, 0.05%, 0.1%, or 0.2% cobalt (e.g., $CoSO_4.7H_2O$) and/or 0.07%, 0.1%, 0.12%, or 0.15% calcium (e.g., $CaCl_2$) and/or 0.0003%, 0.0006%, 0.001%, or 0.0026% selenium (e.g., $Na_2SeO_3$).

The pH of the nutrient media of the invention may vary from about 5.0 to about 7.0. In some embodiments, the pH is within the range of about 6.5 to about 6.7. In some embodiments, the pH is 6.5, 6.6, or 6.7.

2. Fermentation Methods

The media compositions described above may be used in the novel and non-obvious fermentation methods of the invention. The methods of the invention may be carried out using either a solid media or a liquid media, or both. Various modifications of the nutrient media and methods disclosed herein may be made by those skilled in the art, in view of practical and economic considerations, such as the scale of fermentation and local supply of components.

The fermentation method of the invention may be carried out at temperatures ranging from about 18° C. to about 37° C. In some embodiments, the temperatures range from about 18° C. to about 22° C. or from about 24° C. to about 28° C. In some embodiments, the temperatures are 18° C., 20° C., 22° C., 24° C., 26° C., or 28° C.

The fermentation method of the invention may be performed by surface or submerged culture, or a combination of both. In some embodiments, the fermentation is carried out in liquid culture with aeration and agitation. In some embodiments, an anti-foaming agent, such as silicon oil, vegetable oil (e.g., 0.01% soybean oil), or other surfactants, may be added to the liquid cultures of the invention. In some embodiments, the liquid cultures of the invention may be agitated at speeds of about 30 rpm to 130 rpm, and ventilation rates of about 200 to 800 $m^3/h$. In some embodiments, the liquid cultures of the invention may be agitated at speeds of 50, 75, 85, or 100 rpm, and ventilation rates of 300, 500, 650, or 750 $m^3/h$.

The fermentation method of the invention may be initiated in a sterilized flask of media from a slant culture, plate culture, or other source. If a plate culture is used, the culture may be initiated by streaking, spreading, or otherwise plating fungus from a slant culture or other source. The plate culture may be incubated at about 18° C. to about 28° C. for about 4 to 8 days, or until the growth of the fungus is satisfactory, before initiating a liquid seed culture. In some embodiments, the plate culture may be incubated at 18° C. for 4, 5, 6, 7, or 8 days, at 22° C. for 4, 5, 6, 7, or 8 days, at 24° C. for 4, 5, 6, 7, or 8 days, at 26° C. for 4, 5, 6, 7, or 8 days, or at 28° C. for 4, 5, 6, 7, or 8 days. An isolated fungal strain may be used to inoculate the first seed culture, or a mixture of fungal strains may be used.

The method of the invention may involve one or more seed cultures before initiating a large-scale fermentation culture. In some embodiments, the method of the invention involves a single seed culture and a scaled up seed culture. In some embodiments, the seed culture is grown at a temperature of about 18° C. to about 28° C. for about 2 to 10 days, depending on the strain of *Cordyceps sinensis* used, or until growth of the fungus is satisfactory. In some embodiments, the seed culture is incubated at about 18° C. to about 28° C. for about 2 to 4 days. In some embodiments, the seed culture is grown at 18° C. for 2, 3, 4, 5, 6, 7, 8, 9, or 10 days, at 22° C. for 2, 3, 4, 5, 6, 7, 8, 9, or 10 days, at 24° C. for 2, 3, 4, 5, 6, 7, 8, 9, or 10 days, at 24° C. for 2, 3, 4, 5, 6, 7, 8, 9, or 10 days, or at 28° C. for 2, 3, 4, 5, 6, 7, 8, 9, or 10 days.

The seed culture may then be scaled up, and the scaled up seed culture may be incubated at about 18° C. to about 28° C. for about 2 to 10 days, depending on the strain of *Cordyceps sinensis* used, or until the growth of fungus is satisfactory. In some embodiments, the scaled up seed culture is incubated at about 18° C. to about 28° C. for about 2 to 3 days. In some embodiments, the scaled up seed culture is grown at 18° C. for 2, 3, 4, 5, 6, 7, 8, 9, or 10 days, at 22° C. for 2, 3, 4, 5, 6, 7, 8, 9, or 10 days, at 24° C. for 2, 3, 4, 5, 6, 7, 8, 9, or 10 days, or at 28° C. for 2, 3, 4, 5, 6, 7, 8, 9, or 10 days. The scaled up seed culture may then be used to initiate the large-scale fermentation step.

In some embodiments, the seed culture steps may be repeated until there is a sufficient amount of fungus to start the large scale fermentation. Such intermediate stage seed cultures, when used, are developed in essentially the same manner as described above. That is, part of the contents of the flask from the previous seed culture is used to inoculate the medium of the next seed culture and the seed cultures are incubated at about 18° C. to about 28° C. for about 2 to 10 days. However, an advantage of the method of the invention is that it produces large quantities of highly active fungal mycelia using only a single seed culture and scaled up seed culture, as opposed to some prior art methods, which require at least a primary, secondary, and scaled up seed culture before inoculating the large-scale fermentation.

The conditions of the large-scale fermentation step will depend on the particular *Cordyceps sinensis* strain used in the fermentation. For example, if *Paecilomyces hepiali* is used, the large-scale fermentation step may involve incubating the fungus at about 18° C. to about 28° C., 20° C. to 26° C., or 22° C. to 24° C. for any of about 0.5 to 10 days, 1 to 5 days, or 1.5 to 2.5 days. In some embodiments, the large-scale fermentation of *Paecilomyces hepiali* is incubated at 22° C. for 1.8 days, at 24° C. for 1.8 days, at 26° C. for 1.8 days, at 22° C. for 2 days, at 24° C. for 2 days, at 26° C. for 2 days, at 22° C. for 2.3 days, at 24° C. for 2.3 days, or at 26° C. for 2.3 days. Alternatively, if *Hirsutella sinensis* is used, the large-scale fermentation step may involve incubating the fungus at about 18° C. to about 28° C., 20° C. to 26° C., or 22° C. to 24° C. for any of about 1 to 10 days, 3 to 8 days, or 3.5 to 7.5 days. In some embodiments, the large-scale fermentation of *Hirsutella sinensis* is incubated at 18° C. for 3.5 days, at 18° C. for 4.5 days, at 18° C. for 5.5 days, at 18° C. for 6.5 days, at 18° C. for 7.5 days, at 20° C. for 3.5 days, at 20° C. for 4.5 days, at 20° C. for 5.5 days, at 20° C. for 6.5 days, at 20° C. for 7.5 days, at 22° C. for 3.5 days, at 22° C. for 4.5 days, at 22° C. for 5.5 days, at 22° C. for 6.5 days, or at 22° C. for 7.5 days. Alternatively, if *Paecilomyces sinensis* is used, the large scale fermentation step may involve incubating the fungus at about 18° C. to about 28° C., 20° C. to 26° C., or 22° C. to 24° C. for any of about 0.5 to 10 days, 1 to 5 days, or 1.5 to 2.5 days. In some embodiments, the large-scale fermentation of *Paecilomyces sinensis* is incubated at 22° C. for 1.7 days, at 24° C. for 1.8 days, at 26° C. for 1.9 days, at 22° C. for 1.9 days, at 24° C. for 2 days, at 26° C. for 2.1 days, at 22° C. for 2.3 days, at 24° C. for 2.4 days, or at 26° C. for 2.5 days. The resulting mycelia may then be harvested, freeze dried, milled, and/or filtered for use in the formulations of the invention.

In some embodiments, the large scale fermentation may be allowed to continue until a sufficient amount of mycelia is produced. However, an advantage of the method of the invention is that it produces large quantities of highly active fungal mycelia in substantially shorter fermentation times than prior art methods. For example, if *Paecilomyces hepiali* is used, the large scale fermentation may take only 1.5 to 2.3 days, as opposed to prior art methods, which typically require at least 5 to 7 days of large scale fermentation. Similarly, if *Hirsutella sinensis* is used, the large scale fermentation may take only 3 to 8 days, as opposed to prior art methods, which typically require at least 35 to 60 days of large scale fermentation.

The large scale fermentation may be conducted in a suitable container, such as, for example, a stirred tank reactor with means for maintaining a constant temperature, sterilizing the fermentation media and the container, and aerating the fermentation media. In some embodiments, the culture media of the invention is made up in the reactor container and sterilized by heating at temperatures above about 120° C. Upon cooling the container and media to about 18° C. to about 28° C., the sterilized media is inoculated with all or part of the scaled up seed culture and the fermentation is permitted to proceed for a period of time until a sufficient amount of mycelia is produced, while aerating the media.

At the end of the fermentation process, the *Cordyceps sinensis* fermentation products may be isolated and recovered from the culture by any suitable methods known in the art. For example, in one embodiment, the fermentation broth may be drained and discarded, and the solid residue comprising the fungal mycelia may be sterilized by heat, for example, by high pressure steam, and then dried and crushed into a powder. In another embodiment, the mycelia may be freeze dried for about 48 hours and then milled. The resulting powder may be used directly in the various compositions and formulations provided by the present invention. Alternatively, the powder may be further processed, for example, by extraction with organic solvents, such as, 75% ethanol. After evaporation to dryness, the extract may then be used in the various compositions and formulations of the present invention. Alternatively, the organic solvent-extracted fermentation product may be further extracted with water, hot water, organic solvents such as, for example, ether or ethyl acetate, or polar solvents such as, for example, acetone or alcohol. Residual impurities may be removed with solvents such as, for example, petroleum ether or hexane, by adsorptive chromatography with active carbon or silica gel, or by gel filtration through, for example, a SEPHADEX column (Pharmacia). Other methods for removing impurities are known in the art.

Accordingly, in one embodiment, the fermentation method of the invention comprises:
a. inoculating a solid nutrient medium (i.e. a plate culture) with at least one strain of *Cordyceps sinensis* and incubating at about 18° C. to about 28° C. for about 4 to 8 days;
b. inoculating a first liquid nutrient medium (i.e. a seed culture) with at least a portion of the culture from (a) and incubating at about 18° C. to about 28° C. for about 2 to 4 days;
c. inoculating a second liquid nutrient medium (i.e. a scaled up seed culture) with at least a portion of the culture from (b) and incubating at about 18° C. to about 28° C. for about 2 to 3 days;
d. inoculating a third liquid nutrient medium (i.e. a large-scale fermentation culture) with at least a portion of the culture from (c) and incubating at about 18° C. to about 28° C. for about 1 to 3 days or for about 3 to 7 days; and
e. recovering the *Cordyceps sinensis* fermentation product.

An exemplary process of the fermentation method of the invention using *Paecilomyces hepiali* is depicted in FIG. 1.

C. Uses for *Cordyceps sinensis* Fermentation Products

The *Cordyceps sinensis* fermentation products produced by the methods and media of the invention, or obtained by other sources, may be used for treating a mammal afflicted with a variety of diseases, disorders, ailments, and/or symptoms. The fermentation products of the invention may also be used for treating a mammal that may have been exposed to a variety of diseases, disorders, ailments, and/or symptoms.

1. Uses and Formulations for *Cordyceps sinensis* Fermentation Products

The inventors have discovered that *Cordyceps sinensis* fermentation products produced using the methods and media of the invention have increased bioactivities compared to *Cordyceps sinensis* fermentation products produced by other methods. Thus, the *Cordyceps sinensis* fermentation products produced using the method and media of the invention may be used in any therapeutic method known in the art involving *Cordyceps sinensis* fermentation products. The fermentation products, or extracts thereof, may be used in pharmaceutical and dietary compositions containing one or more other components or biologically active agents, such as adjuvants, pharmaceutically acceptable surfactants, excipients, carriers, diluents, vehicles, binding and filling agents, lubricants, disintegrants, wetting agents, suspending agents, emulsifying agents, preservatives, and/or other suitable ingredients. If desired, sweetening, flavoring and/or coloring agents may also be added.

Examples of adjuvants include, for example, alum, MPL, and QS21. Examples of surfactants include, for example, glycerides. Examples of suitable excipients include, but are not limited to, lactose. Examples of binding and filling agents may include, for example, pregelatinized maize starch, polyvinylpyrrolidone, hydroxypropyl methylcellulose, lactose, pentosan, and microcrystalline cellulose or calcium hydrogen phosphate. Examples of lubricants may include, for example, magnesium stearate, talc, or silica. Examples of disintegrants may include, for example, potato starch or sodium starch glycolate. Examples of wetting agents may include, for example, sodium lauryl sulfate. Examples of suspending agents may include, for example, sorbitol syrup, cellulose derivatives, or hydrogenated edible fats. Examples of emulsifying agents may include, for example, lecithin, acacia, almond oil, oily esters, ethyl alcohol, or fractionated vegetable oils. Examples of preservatives may include, for example, methyl or propyl-p-hydroxybenzoates or sorbic acid. Examples of other suitable ingredients may include, but are not limited to, vitamins, antioxidants, amino acids, metal salts, minerals, meat extracts, vegetable extracts, and flavor enhancers.

Pharmaceutical compositions comprising the *Cordyceps sinensis* fermentation products of the invention may be formulated in any dosage form including, for example, powders, granules, capsules, cachets, tablets, dispersions, aqueous or non-aqueous solutions or suspensions, and oil-in water or water-in-oil emulsions. The compositions may be formulated as discrete unit dosage forms with each dose containing a predetermined amount of *Cordyceps sinensis* fermentation product. In some embodiments, the compositions are prepared by uniformly and intimately admixing the active ingredient with liquid carriers or finely divided solid carriers or both, and then, if necessary, shaping the product into the desired presentation. In some embodiments, the formulations are present as a dry product for constitution with water or other suitable vehicle before use. Any methods known to those skilled in the art may be used to formulate and administer the compositions of the invention.

Suitable routes of administration for the pharmaceutical compositions of the invention may include intradermal, transdermal (e.g., slow release polymers), intramuscular, intraperitoneal, intravenous, subcutaneous, oral, epidural, and intranasal routes. Any other convenient route of administration can be used including, for example, infusion or bolus injection, or absorption through epithelial or mucocutaneous linings. In some embodiments, the compositions may be added directly to foods and ingested during normal meals.

2. Formulations and Uses of *Cordyceps sinensis* Fermentation Products for Treating Hepatitis C Infection or Exposure Hepatitis C therapy traditionally includes treatment with interferons, such as interferon-α2A (ROFERON-A, Roche). Current hepatitis C therapy uses a combination of pegylated interferon-α, for example, PEGINTRON (Schering-Plough) or PEGASYS (Roche), and the guanosine analog, ribavirin, for example, REBETOL (Schering-Plough) or COPEGUS (Roche). However, this conventional combination therapy is not fully effective (with only approximately 55% of patients showing a sustained virological response) and its frequent side-effects reduce health-related quality of life in many patients.

The inventors have discovered that *Cordyceps sinensis* fermentation products have a potent adjuvant effect for enhancing the effectiveness of conventional hepatitis C therapies. In one embodiment, the invention relates to adjuvant compositions comprising an effective amount of a *Cordyceps sinensis* fermentation product. The *Cordyceps sinensis* fermentation product used in the adjuvant compositions of the invention may be obtained from any suitable source, or may be produced using the fermentation methods and media described above.

In some embodiments, the *Cordyceps sinensis* fermentation products used in the adjuvant compositions of the invention are from *Paecilomyces hepiali*. In other embodiments, the *Cordyceps sinensis* fermentation products are from *Hirsutella sinensis*. In some embodiments, the adjuvant compositions of the invention further comprise an effective amount of *Astragalus membranaceus* root extract. In some embodiments, the adjuvant compositions of the invention further comprise an effective amount of zinc.

In some embodiments, the adjuvant agent comprises about 50% to about 90% (w/w) of *Cordyceps sinensis* fermentation product, about 10% to about 50% (w/w) of *Astragalus membranaceus* root extract, and/or about 5 to about 10% (w/w) zinc. In some embodiments, the adjuvant agent comprises about 70% to about 80% (w/w) of *Cordyceps sinensis* fermentation product, about 10% to about 30% (w/w) of *Astragalus membranaceus* root extract, and/or about 5% to about 10% (w/w) zinc. In some embodiments, the adjuvant agent comprises about 70% to about 80% (w/w) of *Cordyceps sinensis* fermentation product, about 10% to about 20% (w/w) of *Astragalus membranaceus* root extract, and/or about 5% to about 10% (w/w) zinc. In some embodiments, the adjuvant agent comprises 80% (w/w) of *Cordyceps sinensis* fermentation product, 18% (w/w) of *Astragalus membranaceus* root extract, and 2% (w/w) zinc. In some embodiments, the adjuvant agent comprises 70% (w/w) of *Cordyceps sinensis* fermentation product, 28% (w/w) of *Astragalus membranaceus* root extract, and 2% (w/w) zinc. The adjuvant compositions of the invention may be formulated and administered by any of the methods discussed above.

In other embodiments, the invention relates to methods of treating patients who are infected with hepatitis C and/or patients who may have been exposed to hepatitis C comprising administering to the patient a conventional hepatitis C therapy and an effective amount of an adjuvant composition of the invention. In some embodiments, the conventional hepatitis C therapy comprises an interferon or a pegylated interferon. In some embodiments, the conventional hepatitis C therapy further comprises a guanosine analog such as ribavirin. In some embodiments, the dosage of interferon may be about 50 to about 150 mcg per week and the dosage of ribavirin may be about 800 to about 1200 mg per day.

In some embodiments, the adjuvant compositions of the invention may be formulated in a separate dosage form from the conventional hepatitis C therapeutic agents. In some embodiments, the adjuvant compositions of the invention may be combined with the conventional hepatitis C therapeutic agents into a single dosage form. If the adjuvant agents of the invention and the conventional hepatitis C therapeutic agents are formulated in separate dosage forms, the separate dosage forms may be administered simultaneously, sequentially, or spaced out over a period of time.

The inventors have found that the adjuvant compositions of the invention increase the sustained virologic response attained with conventional hepatitis C therapy and reduce the number and type of adverse effects. This enhancing effect of the adjuvant agents of the invention was particularly pronounced in patients with cirrhosis. Without being bound by theory, it is believed that the interferon component of conventional therapy kills hepatitis C virus and the adjuvant agent serves to boost the immune system by increasing levels of IgG and IgA, and by increasing the $CD4^+/CD8^+$ cell ratio.

EXAMPLES

Reference will now be made in detail to specific embodiments of the invention. While the invention will be described in conjunction with these embodiments, it will be understood that the invention is not limited to those embodiments. On the contrary, the invention is intended to cover alternatives, modifications, and equivalents, which may be included within the invention as defined by the appended claims.

A. Adjuvant Preparation

1. *Hirsutella sinensis* Fermentation

The *Hirsutella sinensis* mycelia used in the experiments discussed below were produced by the following method.

The *Hirsutella sinensis* strain was purified from natural fresh *Cordyceps sinensis* obtained from Mainland China. The strain was plate-cultured for 30 days at 18° C. on solid medium containing the components discussed below for the seed culture media plus 2.0% agar.

A series of sequential liquid cultures and fermentations were then performed over a period of about 27 days.

1. The seed culture was prepared as follows:

Culture media (a total of 0.6 L in water):

| | |
|---|---|
| sucrose | 24 g |
| $(NH_4)_2HPO_4$ | 0.15 g |
| $KH_2PO_4$ | 0.6 g |
| $K_2HPO_4$ | 1.38 g |
| $MgSO_4 \cdot 7H_2O$ | 0.3 g |
| KCl | 0.3 g |
| $MnSO_4$ | 0.6 g |
| $CuSO_4 5 \cdot H_2O$ | 0.0096 g |
| $FeSO_4 \cdot 7H_2O$ | 0.6 g |
| $CaCl_2$ | 0.9 g |
| $NaSeO_3$ | 0.0072 g |

6 flasks (size 250 mL) were each filled with 100 mL culture media. The flasks containing the media were sterilized, cooled to 18° C., and adjusted to pH 6.5. Each flask was inoculated with *Hirsutella sinensis* strain from a plate culture. The inoculated cultures were incubated for 10 days at 18° C., in a shaking incubator at a speed of 175 rpm.

2. The scaled up seed culture was prepared as follows:

Culture media (a total of 6 L in water):

| | |
|---|---|
| sucrose | 240 g |
| $(NH_4)_2HPO_4$ | 1.5 g |
| $KH_2PO_4$ | 6 g |
| $K_2HPO_4$ | 13.8 g |
| $MgSO_4 \cdot 7H_2O$ | 3 g |
| KCl | 3 g |
| $MnSO_4$ | 6 g |
| $CuSO_4 \cdot 5H_2O$ | 0.096 g |
| $FeSO_4 \cdot 7H_2O$ | 6 g |
| $CaCl_2$ | 9 g |
| $NaSeO_3$ | 0.072 g |

6 flasks (size 3 L) were each filled with 1000 mL culture media. The flasks containing the media were sterilized, cooled to 18° C., and adjusted to pH 6.5. Each flask was inoculated with the *Hirsutella sinensis* strain from the seed culture. The inoculated cultures were incubated for 10 days at 18° C., in a shaking incubator at a speed of 130 rpm.

3. The fermentation steps were carried out as follows (note, however, that the mycelium product produced in any of the following fermentation steps may be used as raw material for the adjuvant agents of the invention, since the main difference among the three fermentation steps is the amount of raw material produced):

Small Scale Fermentation Culture: Fermentation media (a total of 40 L in water in a 100 L fermentor chamber):

| | |
|---|---|
| sucrose | 1600 g |
| $(NH_4)_2HPO_4$ | 10 g |

-continued

| | |
|---|---|
| $KH_2PO_4$ | 40 g |
| $K_2HPO_4$ | 92 g |
| $MgSO_4 \cdot 7H_2O$ | 20 g |
| KCl | 20 g |
| $MnSO_4$ | 40 g |
| $CuSO_4 \cdot 5H_2O$ | 0.64 g |
| $FeSO_4 \cdot 7H_2O$ | 40 g |
| $CaCl_2$ | 60 g |
| $NaSeO_3$ | 0.48 g |

The fermentation chamber containing the culture media was sterilized, cooled to 18° C., and adjusted to pH 6.5. The media was inoculated with the *Hirsutella sinensis* strain from the scaled up seed culture by adding the 6 L scale-up seed culture to the fermentor chamber. The inoculated cultures were incubated for 7 days at 18° C. with a stir-speed of 80-200 rpm.

Middle Scale Fermentation Culture: Fermentation media (a total of 500 L in water in a 1000 L fermentor chamber):

| | |
|---|---|
| sucrose | 20 kg |
| $(NH_4)_2HPO_4$ | 125 g |
| $KH_2PO_4$ | 500 g |
| $K_2HPO_4$ | 1150 g |
| $MgSO_4 \cdot 7H_2O$ | 250 g |
| KCl | 250 g |
| $MnSO_4$ | 500 g |
| $CuSO_4 \cdot 5H_2O$ | 8 g |
| $FeSO_4 \cdot 7H_2O$ | 500 g |
| $CaCl_2$ | 750 g |
| $NaSeO_3$ | 6 g |

The fermentation chamber containing the culture media was sterilized, cooled to 18° C., and adjusted to pH 6.5. The media was inoculated with the *Hirsutella sinensis* strain from the 100 L fermentor chamber. The inoculated cultures were incubated for 5 days at 18° C. with a stir-speed of 50-80 rpm.

Large-Scale Fermentation Culture: Fermentation media (a total of 8000 L in water in a 10000 L fermentor chamber):

| | |
|---|---|
| sucrose | 320 kg |
| $(NH_4)_2HPO_4$ | 2000 g |
| $KH_2PO_4$ | 8000 g |
| $K_2HPO_4$ | 18.4 kg |
| $MgSO_4 \cdot 7H_2O$ | 4000 g |
| KCl | 4000 g |
| $MnSO_4$ | 8000 g |
| $CuSO_4 \cdot 5H_2O$ | 128 g |
| $FeSO_4 \cdot 7H_2O$ | 8000 g |
| $CaCl_2$ | 12 kg |
| $NaSeO_3$ | 96 g |

The fermentation chamber containing the culture media was sterilized, cooled to 18° C., and adjusted to pH 6.5. The media was inoculated with the *Hirsutella sinensis* strain from the 1000 L fermentor chamber. The inoculated cultures were incubated for 4 days at 18° C. with a stir-speed of 40-70 rpm. The fermented culture medium (broth) was separated from the solid product, and a mycelia cake was produced using a plate and frame filter press. The water was then removed from the mycelia cake by freeze-drying.

A comparison between the method of the invention for producing *Hirsutella sinensis* mycelia and the method disclosed in U.S. application Ser. No. 11/450,747 is shown as Table 1.

TABLE 1

Comparison between the method of the invention for producing
*Hirsutella sinensis* mycelia and the method disclosed in
U.S. Application No. 11/450,747

|  | Method of the Invention | U.S. Application No. 11/450,747 |
|---|---|---|
| Plate culture | 3 generations (10 days/generation) 30 days 18° C. pH 6.5 Solid medium as shown above | >10 generations (10 days/generation) >100 days >5 generations at 0-10° C. pH 8 Solid medium containing beef tea, lactalbumin hydrolysate, yeast powder, glucose, milk, nucleic acid, magnesium sulfate, sodium dihydrogen phosphate, and vitamins |
| Seed cultures in rocking device (shaker) (liquid medium) | Culturing a seed culture for 10 days; Culturing a scaled up seed culture for 10 days; 18° C. pH 6.5 Liquid medium as shown above | Culturing a seed culture for 12 days The culture volume is then expanded 8-fold and fermented stepwise before transfer into a vat fermentor 18° C. pH 7.5 Liquid medium containing silk worm chrysalis powder, protein peptone, corn flour, wheat gluten, glucose, magnesium sulfate, and dipotassium hydrogen phosphate |
| Fermentation culture in vat fermentor (liquid medium) | 3-7 days for each fermentation culture expansion step Small Scale Fermentation Culture: 7 days Middle Scale Fermentation Culture: 5 days Large Scale Fermentation Culture: 4 days (Total: 16 days) 18° C. pH 6.5 Liquid medium as shown above Expansion: 15-20 times the seed culture media volume | 12 days for each fermentation culture step Small Scale Fermentation Culture: 12 days Middle Scale Fermentation Culture: 12 days Large Scale Fermentation Culture: 12 days (Total: 36 days) 18° C. pH 7.5 Liquid medium containing silk worm chrysalis powder, protein peptone, corn flour, wheat gluten, glucose, magnesium sulfate, and dipotassium hydrogen phosphate Expansion: 8 times the seed culture media volume |

The advantages of the method of the invention over prior art methods are as follows:
a) the method of the invention involves growing the fungus for only 3 generations in the plate culture stage, whereas the method of the '747 application requires more than 10 generations; and
b) the method of the invention involves fermenting the fungus for only 3-7 days in media that is 15 to 20 times the volume of the serial fermenting cultures, whereas the fermentation step of the '747 application requires 12 days in media that is only 8 to 10 times the volume of the serial fermenting cultures.

Without being bound by theory, it is believed that the advantages of the method of the invention are due to the operating pH and the novel formulation of the media used, including the use of specialized trace elements. The advantages of the method of the invention over prior art methods reduce the cost and time of producing *Cordyceps sinensis* mycelia and also increase the bioactivity of the mycelia, as discussed in greater detail below.

2. *Paecilomyces hepiali* Fermentation

The *Paecilomyces hepiali* mycelia used in the clinical trials discussed below were produced by the following method.

The *Paecilomyces hepiali* strain was purified from natural fresh *Cordyceps sinensis* obtained from Mainland China. The strain was plate-cultured for 7 days at 24° C. on solid medium containing the components discussed below for the seed culture media plus 2.0% agar.

A series of sequential liquid cultures and fermentations were then performed over a period of about 9 days.

1. The seed culture was prepared as follows:
Culture media (a total of 0.8 L in water):

| sucrose | 16 g |
|---|---|
| glucose | 16 g |
| yeast powder | 2.4 g |
| $KH_2PO_4$ | 0.8 g |
| $MgSO_4 \cdot 7H_2O$ | 4 g |
| KCl | 0.4 g |
| $MnSO_4$ | 0.6 g |
| $CuSO_4 \cdot 5H_2O$ | 0.0256 g |
| $FeSO_4 \cdot 7H_2O$ | 0.6 g |
| $CaCl_2$ | 0.24 g |
| $NaSeO_3$ | 0.0096 g |

8 flasks (size 250 mL) were each filled with 100 mL culture media. The flasks containing the media were sterilized, cooled to 24° C., and adjusted to pH 6.5. Each flask was inoculated with a *Paecilomyces hepiali* strain from a plate culture. The inoculated cultures were incubated for 4 days at 24° C., in a shaking incubator at a speed of 175 rpm.

2. The scaled up seed culture was prepared as follows:
Culture media (a total of 8 L in water):

| sucrose | 160 g |
|---|---|
| glucose | 160 g |
| yeast powder | 24 g |
| $KH_2PO_4$ | 8 g |
| $MgSO_4 \cdot 7H_2O$ | 40 g |
| KCl | 4 g |
| $MnSO_4$ | 6 g |
| $CuSO_4 \cdot 5H_2O$ | 0.256 g |
| $FeSO_4 \cdot 7H_2O$ | 6 g |
| $CaCl_2$ | 24 g |
| $NaSeO_3$ | 0.096 g |

8 flasks (size 3 L) were each filled with 1000 mL culture media. The flasks containing the media were sterilized, cooled to 24° C., and adjusted to pH 6.5. Each flask was inoculated with the *Paecilomyces hepiali* strain from the seed culture. The inoculated cultures were incubated for 3 days at 24° C., in a shaking incubator at a speed of 145 rpm.

3. The large scale fermentation was carried out as follows:
Fermentation media (a total of 8000 L in water in a 10000 L fermentor chamber):

| sucrose | 160000 g |
|---|---|
| glucose | 160000 g |
| yeast powder | 24000 g |
| $KH_2PO_4$ | 8000 g |
| $MgSO_4 \cdot 7H_2O$ | 40000 g |
| KCl | 4000 g |
| $MnSO_4$ | 6000 g |
| $CuSO_4 \cdot 5H_2O$ | 256 g |
| $FeSO_4 \cdot 7H_2O$ | 6000 g |
| $CaCl_2$ | 24000 g |
| $NaSeO_3$ | 96 g |

The fermentor chamber containing the culture media was sterilized, cooled to 24° C., and adjusted to pH 6.5. The media was inoculated with the *Paecilomyces hepiali* strain from the scaled up seed culture by adding the 6 L scaled up seed culture to the fermentor chamber. The inoculated cultures were incubated for 2 days at 24° C. with a stir-speed of 50-100 rpm. The fermented culture medium (broth) was separated from the solid product, and a mycelia cake was produced using a plate and frame filter press. The water was then removed from the mycelia cake by freeze-drying.

A comparison between the method of the invention for producing the *Paecilomyces hepiali* mycelia and the method disclosed in PCT/CN98/00258 is shown as Table 2.

TABLE 2

Comparison between the method of the invention for producing the *Paecilomyces hepiali* mycelia and the method disclosed in PCT/CN98/00258

| | Method of the Invention | PCT/CN98/00258 |
|---|---|---|
| plate culture | 7 days<br>24° C.<br>pH 6.5<br>Solid medium as shown above | 5-6 days<br>25° C.<br>pH 6.4<br>Compostion of culture media not avaliable |
| Seed cultures in rocking device (shaker) (liquid medium) | Culturing a seed culture for 4 days;<br>Culturing a scaled up seed culture for 3 days;<br>24° C.<br>pH 6.5<br>Liquid medium as shown above | Culturing a primary seed culture for 5-6 days;<br>Culturing a secondary seed culture for 4 days;<br>Culturing a scaled up seed culture for 4 days; and<br>25° C.<br>pH 6.4<br>Liquid medium containing glucose, sucrose, peptone, bran, potassium dihydrogen phosphate, magnesium sulfate |
| Fermentation culture in vat fermentor (liquid medium) | 2 days in a 10000 L vat fermentor directly from seed culture<br>24° C.<br>pH 6.5<br>Liquid medium as shown above<br>Expansion: 1300~1400 times the seed culture media volume | 5-6 days for each fermentation culture expansion step<br>The culture volume is expanded and fermented step-wise until a 2000 L vat fermentor volume is reached<br>24-25° C.<br>pH 6.4<br>Liquid medium containing glucose, sucrose, powder of soya-bean cake, bran, potassium dihydrogen phosphate, magnesium sulfate, soya-bean oil<br>Expansion: 10 times the seed culture media volume |

The major advantages of the method of the invention over prior art methods are as follows:

a) the method of the invention involves fermenting the fungus in a vat for only 2 days, whereas the method of the PCT/CN98/00258 requires 5-6 days; and b) the method of the invention allows the total volume to be expanded about 1300-1400 times, whereas the method of the PCT/CN98/00258 involves only a 10-fold expansion of culture volume.

The *Paecilomyces hepiali* mycelia produced by the foregoing method ("Mycelia") were compared to a commercially available *Paecilomyces hepiali* mycelia preparation, CordyMax Cs-4, NUSKIN ("CordyMax"). The total nucleosides, polysaccharide, superoxide dismutases, and total free amino acids were analyzed by HPLC, ethanol participation, spectrophotometer, and amino acid analyzer, respectively. Table 3 presents the results of this analysis.

TABLE 3

Comparison between the compositions of mycelium produced by the method of the invention and CordyMax Cs-4 mycelium

| Component | Mycelia | CordyMax |
|---|---|---|
| Total nucleoside (Adenosine) | 1.8% (0.4%) | 0.7% (0.1%) |
| Total Polysaccharide | 9% | 6% |
| Superoxide dismutases (SOD) | $4 \times 10^3$ U/g | $2 \times 10^3$ U/g |
| Total Free Amino Acid (mg/100 g) | 20300 | 3800 |
| L-Threonine* | 620 | 75 |
| L-Valine* | 720 | 330 |
| L-Methionine* | 350 | 35 |
| L-Isoleucine* | 670 | 110 |
| L-Leucine* | 1400 | 110 |
| L-Phenylalanine* | 860 | 30 |
| Tryptophan* | 260 | 28 |
| L-Lysine* | 1400 | 250 |
| L-Arginine# | 1000 | 120 |
| L-Histidine# | N.D. | 100 |
| γ-Aminobutyric Acid | 1830 | 250 |
| o-Phosphorserine | 80 | N.D. |
| Taurine | 18 | 70 |
| o-Phosphoethanolamine | 62 | 70 |
| Urea | N.D. | N.D. |
| L-Aspartic Acid | 740 | 130 |
| L-Serine | 720 | 64 |
| Asparagine | 650 | N.D. |
| L-Glutamic acid | 670 | 800 |
| Sarcosine | N.D. | N.D. |
| L-2-Aminoadipic Acid | 160 | 26 |
| Glycine | 530 | 97 |
| L-Alanine | 1500 | 400 |
| L-Citrulline | 1100 | N.D. |
| DL-2-Aminobutyric Acid | 40 | 25 |
| L(−)-Proline | 1600 | 250 |
| L(−)-Cystine | 140 | N.D. |
| L-Cystathionine | 95 | 57 |
| L-Tyrosine | 680 | 140 |
| β-Alanine | N.D. | 30 |
| DL-3-Aminoisobutyric Acid | 74 | 19 |
| Ethanolamine | 100 | 18 |
| DL-plus allo-δ-Hydroxylysine | 56 | 15 |
| L-Ornithine | 530 | 69 |
| L-1-Methylhistidine | 400 | N.D. |
| L-3-Methylhistidine | N.D. | N.D. |
| L-Anserine | 1300 | 100 |
| L-Carnosine | 170 | N.D. |
| L-Hydroxyproline | N.D. | N.D. |

*Essential amino acid
Semi-Essential amino acid
N.D. = not determined

These data demonstrate that the *Paecilomyces hepiali* mycelia produced by the method of the invention contain greater quantities of functional ingredients than *Paecilomyces hepiali* mycelia produced by prior art methods.

3. *Astragalus membranaceus* Extraction

Dried root of *Astraglus membranaceus* (Fisch.) Bge. (Shaanxi, China) was extracted with hot water twice at a 1:10 (v/v) ratio and centrifuged to remove the particulate material. The extraction fluids were combined, concentrated, and spray-dried. The extraction ratio, i.e., the weight ratio of raw material (dried of *Astraglus membranaceus*) to the extracted powder, was about 2 to 5.

4. Adjuvant Formulation

The adjuvant compositions used in the examples discussed below were prepared as follows.

50-90% (w/w) of fermented *Cordyceps sinensis* powder, 10-50% of extracted *Astraglus membranaceus* powder, and/or 5-10% of zinc were placed into a U-type granulator and mixed for 3 minutes. Water was added and the combination was kneaded to produce a wet granule. After drying the wet granule in an oven at 50° C. for 8 hrs, the granule was sealed in a drum and cooled to room temperature. The dry granule was sieved through an 0.8 mm mesh and mixed in a tumbler for 6 minutes with the following excipients: Povidone K-90 (Polyvinylpyrrolidone K-90; Poly[1-(2-oxo-1-pyrrolidinyl) ethylene], CORUM), calcium phosphate dibasic (Sigma), Crospovidone XL (CORUM), magnesium stearate (Merck), Opadry II (Colorcon), and ariable yellow (BASF). The mixed powder was tableted and packaged with press through packaging (PTP, U.M. GRAVURE).

B. Animal Safety Studies 1. 14 Day Subacute Toxicity Study

Rats were administered water extracts of the *Hirsutella sinensis* mycelia described above ("Mycelia") or vehicle control ("Control") once daily by oral gavage for 14 days. The amount of extract used in this study (5 g/kg) was equivalent to 10-times the recommended dose for humans. The dependent variables examined in this study were: (1) behavior (active contraction); (2) body weight and intake of food and water; (3) hematology parameters, such as hemochrome, thrombocyte, red blood cell, hemoleukocyte, and clotting time; (4) clinical chemistry, such as bilirubin, AST, ALT, BUN, creatinine, glucose, total protein, albumin, K, Na, Ca; (5) urinalysis, such as settling rate, protein, electrolytic containing pH value; and (6) histopathology, such as heat, liver, lung, kidney, stomach, and cholecyst. The results are shown in Table 4 (data are presented as the average of each test group±the standard deviation).

Among the dependent variables, including the body weight and intake of food and water, there was no statistically significant difference between the treatment and the control groups. These results indicate that under the conditions used in this experiment, the water extracts of *Hirsutella sinensis* mycelia were not toxic to rats.

2. 90 Day Subacute Toxicity Study

Rats were administrated water extracts of the *Paecilomyces hepiali* mycelia described above or vehicle control once daily by oral gavage for 90 days. Three experimental groups were examined: (1) control ("Control"); (2) 2500 mg/kg dosing ("Mycelia 2500"); and (3) 7500 mg/kg dosing ("Mycelia 7500"). The amount of extract used in experimental groups 2 and 3 was equivalent to 100 times and 300 times the recommended dose for humans, respectively. The dependent variables examined in this study were: (1) mortality; (2) clinical observations; (3) body weight; (4) food consumption; (5) hematology parameters, such as Hb, HCT, PLT, RBC, and WBC; (6) clinical chemistry, such as ALT, TP, BUN, Cre, and Glu; and (7) histopathology, such as heart, liver, lung, kidney, and stomach. The results are shown in Table 5 (data are presented as the average of each test group±the standard deviation).

TABLE 5

Results of 90 day subacute toxicity study examining the effects of *Paecilomyces hepiali* mycelia on rats

| Variable | Control | Mycelia 2500 | Mycelia 7500 |
|---|---|---|---|
| Body weight change | 414 g ± 11.5 g | 416 g ± 21.5 g | 412.5 g ± 25 g |
| Hb | 13.6 g/dL ± 0.25 g/dL | 14.35 g/dL ± 0.2 g/dL | 13.85 g/dL ± 0.3 g/dL |
| HCT | 38.58% ± 0.83% | 40.5% ± 0.5% | 40.25% ± 0.7% |
| PLT | 843.5 sec ± 37.5 sec | 921 sec ± 44 sec | 781 sec ± 19 sec |
| RBC | $7.45 \times 10^6/\mu L \pm 0.06 \times 10^6/\mu L$ | $7.8 \times 10^6/\mu L \pm 0.04 \times 10^6/\mu L$ | $7.65 \times 10^6/\mu L \pm 0.06 \times 10^6/\mu L$ |
| WBC | $4.6 \times 10^3/\mu L \pm 0.6 \times 10^3/\mu L$ | $4 \times 10^3/\mu L \pm 0.5 \times 10^3/\mu L$ | $5.15 \; 10^3/\mu L \pm 0.45 \; 10^3/\mu L$ |
| ALT | 54.5 U/L ± 4.25 U/L | 52.5 U/L ± 4.45 U/L | 60 U/L ± 4.5 U/L |
| TP | 6.46 g/dL ± 0.35 g/dL | 6.5 g/dL ± 0.3 g/dL | 6.52 g/dL ± 0.35 g/dL |
| BUN | 22 mg/dL ± 3.05 mg/dL | 18.55 mg/dL ± 2.95 mg/dL | 18 mg/dL ± 0.315 mg/dL |
| Cre | 0.43 mg/dL ± 0.02 mg/dL | 0.4 mg/dL ± 0.02 mg/dL | 0.44 mg/dL ± 0.03 mg/dL |
| Glu | 155.5 mg/dL ± 6.45 mg/dL | 144 mg/dL ± 5.05 mg/dL | 152.5 mg/dL ± 4.4 mg/dL |

TABLE 4

Results of 14 day subacute toxicity study examining the effects of *Hirsutella sinensis* mycelia on rats

| Variable | Control | Mycelia |
|---|---|---|
| Body weight change | 36.9 g ± 3.3 g | 41.8 g ± 9.0 g |
| Food consumption | 26.7 g ± 0.7 g | 26.6 g ± 2.0 g |
| Water intake | 46.2 g ± 1.1 g | 42.7 g ± 5.0 g |
| Hb | 12.8 g/dL ± 0.2 g/dL | 12.9 g/dL ± 0.3 g/dL |
| WBC | $8.9 \times 10^3/\mu L \pm 0.5 \times 10^3/\mu L$ | $9.8 \times 10^3/\mu L \pm 0.8 \times 10^3/\mu L$ |
| ALB | 3.2 mg/dL ± 0.2 mg/dL | 3.2 mg/dL ± 0.1 mg/dL |
| BUN | 18 mg/dL ± 0.05 mg/dL | 18.9 mg/dL ± 1.5 mg/dL |

Among the dependent variables, there was no significant difference between the treatment and the control groups. These results indicate that under the conditions used in this experiment, the water extracts of *Paecilomyces hepiali* mycelia were not toxic to rats.

C. Bioassay Experiments

Human peripheral blood mononuclear cells (PBMCs) were suspended in RPMI ($6 \times 10^6$ cells/mL; Sigma) supplemented with 5% fetal calf serum (FCS) and penicillin/streptomycin/glutamine (PSG) and were incubated at 37° C. and 5% $CO_2$ for 16 hours with 5 µg/mL Brefeldin A and 50 µg/mL of *Paecilomyces hepiali* mycelia obtained from five different sources: (1) Pharmanex; (2) Formosa Kingstone Bioproducts Int'l Corp.; (3) GeneFerm Biotechnology Co. Ltd.; (4) Green Strong Corp.; and (5) the method of the invention. Negative control cells were incubated with PBS, and positive control cells were incubated with phorbol myristate acetate (PMA) plus ionomycine. After incubation, the PBMCs were harvested, suspended in two 1.5 mL tubes, and incubated with anti-CD4 antibodies (anti-CD4 clone RPA-T4, BD Pharmingen) or anti-CD8 antibodies (anti-CD8 clone HIT8a, 8D Pharmingen) at 4° C. for 30 min in the dark. The cells were washed with 5% FCS and then incubated with Cytofix/Cytoperm™ (BD Pharmingen) for 20 minutes at 4° C. The cells were then washed once with 250 μL of 1×Perm/Wash (BD Pharmingen). Intracellular cytokines were stained with anti-human IL-2 antibody (clone MQ1-17H12, BD Pharmingen) or anti-IFN-γ antibody (clone 4S.B3, BD Pharmingen) at 4° C. for 30 minutes in the dark. After washing with 5% FCS, the number of IL-2 or IFN-γ positive cells (as a % of $CD4^+$ or $CD8^+$ cells, respectively) was detected by flow cytometry. Table 6 presents the results of this experiment (control data was set to 1 and all other data is shown relative to the control).

TABLE 6

Relative number of IL-2 and IFN-γ positive cells after treatment with Paecilomyces hepiali mycelia from different sources

| | Negative Control | Positive Control | Pharmanex | Formosa | GeneFerm | Green Strong | Method of Invention |
|---|---|---|---|---|---|---|---|
| $CD4^+/IL-2^+$ | 1 | 15 | 5 | 7 | 10 | 6 | 19 |
| $CD8^+/IFN-\gamma^+$ | 1 | 20 | 3 | 4 | 6 | 6 | 10 |

The $CD4^+$/IL-2 data demonstrate that Paecilomyces hepiali mycelia produced by the method of the invention show the highest potency for immune-stimulation and are around 2 to 4 times more potent than Paecilomyces hepiali mycelia from other sources. The CD8+/IFNγ data confirm that the mycelia of the invention have the highest potency for immune-stimulation, and are around 1.5 to 3 times more potent than mycelia from other sources. Since $CD4^+$/IL-2 and CD8+/IFNγ data are good indicators of the ability to kill hepatitis C virus in the liver, these results suggest that the mycelia of the invention have greater antiviral activity than mycelia from other sources.

The experimental protocol described above was used to compare the bioactivities of Paecilomyces hepiali mycelia produced by the method of the invention with Hirsutella sinensis mycelia produced by the method of the invention. The results are shown in Table 7 (control data was set to 1 and all other data is shown relative to the control).

TABLE 7

Relative number of IL-2 and IFN-γ positive cells after treatment with Hirsutella sinensis or Paecilomyces hepiali mycelia

| | PBS Control | Positive Control | P.h. | H.s. |
|---|---|---|---|---|
| $CD4^+/IL-2^+$ | 1.00 | 34.6 | 9.4 | 2.9 |
| $CD8^+/IFN-\gamma^+$ | 1.00 | 42.6 | 10.4 | 3.8 |

The results demonstrate that Paecilomyces hepiali mycelia produced by the method of the invention have a higher potency for immune-stimulation than Hirsutella sinensis mycelia produced by the method of the invention.

In order to investigate the therapeutic effects of Paecilomyces hepiali mycelia combined with Astragalus membranaceus extract, two experiments were performed. In the first study, the experimental protocol described above was used to examine the immune-stimulation of Paecilomyces hepiali mycelia produced by the method of the invention compared to the immune-stimulation of Paecilomyces hepiali mycelia produced by the method of the invention combined with Astragalus membranaceus extract. The results of this experiment are presented in Table 8 (control data was set to 1 and all other data is shown relative to the control).

TABLE 8

Relative number of IL-2 and IFN-γ positive cells after treatment with Paecilomyces hepiali mycelia with or without Astragalus membranaceus extract

| | PBS Control | Positive Control | Mycelia Alone | Mycelia + Extract |
|---|---|---|---|---|
| $CD4^+/IL-2^+$ | 1 | 21 | 15 | 17 |
| $CD8^+/IFN-\gamma^+$ | 1 | 19 | 10 | 11 |

The $CD4^+$/IL-2 data demonstrate that the combination of Paecilomyces hepiali mycelia produced by the method of the invention and Astragalus membranaceus extract has a higher potency for immune-stimulation than Paecilomyces hepiali mycelia alone.

The second experiment examined the superoxide scavenging activity of Paecilomyces hepiali mycelia produced by the method of the invention compared to the superoxide scavenging activity of Paecilomyces hepiali mycelia produced by the method of the invention combined with Astragalus membranaceus extract. Superoxide scavenging activity is indicative of an ability to prevent liver damage caused by free radicals. The superoxide scavenging activity was analyzed by nitroblue tetrazolium chloride (NBT) assay. NBT absorbs superoxide and changes the color of the reaction solution to purple, which is absorbed at 560 nm. 25 μl of test sample or superoxide dismutase (SOD) standard ("positive control") was added to each well in a 96-well plate and 63 μM NBT, 300 μM xanthine, and 0.03 U/ml xanthine oxidase (each obtained from Sigma) were added. The absorbance at 560 nm was measured at 1 minute intervals for 5 minutes total. Table 9 presents the results of this study (control data was set to 1 and all other data is shown relative to the control).

TABLE 9

Relative levels of superoxide dismutase activity after treatment with Paecilomyces hepiali mycelia with or without Astragalus membranaceus extract

| | Positive Control | Mycelia Alone | Mycelia + Extract |
|---|---|---|---|
| SOD (U/mg) | 1.00 | 0.468 | 2.384 |

These results show that the combination of Paecilomyces hepialimycelia produced by the method of the invention and

*Astragalus membranaceus* extract has a 5-fold higher superoxide scavenging activity (antioxidant activity) than *Paecilomyces hepiali* mycelia alone. Thus, adjuvant agent of the invention comprising *Astragalus membranaceus* and *Paecilomyces hepiali* mycelia has higher potency, and may exhibit therapeutic synergy compared to adjuvant agents comprising *Paecilomyces hepiali* mycelia without *Astragalus membranaceus*.

D. Hepatitis C Clinical Trials 1-3

Three double-blinded clinical trials were conducted to examine the effects of the adjuvant agent of the invention comprising *Hirsutella sinensis* mycelia and *Astragalus membranaceus* extract for treating hepatitis C patients. Patients were treated with α-interferon, with or without ribavirin, for one week and on the second week, the patients were randomly assigned into two groups. The two groups were treated with the adjuvant agent of the invention or placebo concurrently with α-interferon, with or without ribavirin, for 24 weeks, and then with the adjuvant agent of the invention without α-interferon and ribavirin for another 24 weeks. Blood samples were collected and any side effects were documented throughout the experiment period. The dependent variables examined were: (1) blood chemistry: WBC, hemoglobin, platelet, BUN, creatinine, SGOT/SGPT, and HCV-RNA; and (2) occurrence of side effects.

Experimental conditions and results of the individual clinical trials are described below.

1. Clinical Trial #1

A total 28 patients infected with hepatitis C were treated with interferon-α 2A (ROFERON-A, Roche, "IFN") at 3 MU subcutaneously 3 times per week for 6 months. All patients recruited in this study had not been previously treated with ROFERON-A. On the second week, the patients were randomly assigned into two groups and either treated with the adjuvant agent of the invention (N=10) at 3180 mg (about 70% to 80% (w/w) of *Hirsutella sinensis* mycelia, about 10% to 20% (w/w) of *Astragalus membranaceus* extract, and about 5% to 10% of zinc) per day or placebo (N=18, adjuvant agent in which the active raw materials were replaced with microcrystalline cellulose) concurrently with ROFERON-A until the treatment was completed. After treatment was finished, the patients were examined again in follow-up visits at 6 and 12 months.

Serum samples from each patient were analyzed for the presence of HCV RNA using a LightCycler-RNA Amplification Kit SYBR Green I (Roche Diagnostics GmbH). Each 20 μL of the PCR mixture contained LightCycler-RT-PCR Buffer, SYBR Green (Roche), 5 mM $MgCl_2$, 0.25 μM forward primer (5'-GAGGAACTACTGTCTTCACGCAGAA-3'), 0.5 μM reverse primer (5'-CTTTCGCGACCCAACAC-TACTC-3'), LightCycler-RT-PCR Enzyme Mix, and template RNA. RT-PCR amplification was performed using a 10 min cycle at 55° C. to allow for reverse transcription, followed by a 30 sec cycle at 95° C. to allow for denaturation, followed by 45 cycles at 95° C. for 5 sec, 55° C. for 10 sec, 72° C. for 13 sec, and 85° C. for 5 sec to allow for amplification. All reactions were performed in a LightCycler (Roche Diagnostics GmbH).

Table 10 summarizes the results for these patients. "Response" is defined as the percentage of patients who showed no detectable levels of HCV RNA.

TABLE 10

Patients showing no detectable levels of HCV RNA after treatment with IFN with adjuvant agent of the invention or placebo

| | Response | | | |
|---|---|---|---|---|
| Group | 3 Months | 6 Months | 6 Months Post Treatment | 12 Months Post Treatment |
| IFN + adjuvant | 4/10 (40%) | 7/10 (70%) | 7/10 (70%)* | 7/10 (70%) |
| IFN + placebo | 10/18 (55.5%) | 6/18 (33.3%) | 2/18 (11.1%)* | 2/18 (11.1%) |

*SVR

These results show that: (1) the adjuvant agent enhanced the therapeutic effect of IFN; and (2) the recurrence of hepatitis C was lower in the group treated with the adjuvant agent than the placebo group.

2. Clinical Trial #2

A total 20 patients infected with hepatitis C were treated with interferon-α 2A (ROFERON-A, Roche, "IFN") at 3 MU, three times a week subcutaneously and ribavirin (COPEGUS, Roche, "ribavirin") at 1000 mg, twice a week for 6 months. All patients recruited in this study had not been previously treated with ROFERON-A or COPEGUS. On the second week, the patients were randomly assigned into two groups treated with the adjuvant agent of the invention at 3180 mg (about 70% to 80% (w/w) of *Hirsutella sinensis* mycelia, about 10% to 20% (w/w) of *Astragalus membranaceus* extract, and about 5% to 10% of zinc) per day (N=8) or placebo (N=12, adjuvant agent in which the active raw materials were replaced with microcrystalline cellulose) concurrently with ROFERON-A and COPEGUS until the treatment was completed. The patients were examined again in follow-up visits at 6 and 12 months.

Serum samples from each patient were analyzed for the presence of HCV RNA as discussed above. Table 11 summarizes the results for these patients ("response" is defined as the percentage of patients who showed no detectable levels of HCV RNA).

TABLE 11

Patients showing no detectable levels of HCV RNA after treatment with IFN and ribavirin with adjuvant agent of the invention or placebo

| | Response | | | |
|---|---|---|---|---|
| Group | 3 Months | 6 Months | 6 Months Post Treatment | 12 Months Post Treatment |
| IFN + ribavirin + adjuvant | 3/8 (7.5%) | 7/8 (87.5%) | 7/8 (87.5%)* | 7/8 (87.5%) |
| IFN + ribavirin + placebo | 0/12 (0%) | 2/12 (16.7%) | 2/12 (16.7%)* | 0/12 (0%) |

*SVR

These results show that: (1) the adjuvant agent enhanced the therapeutic effect of the combination therapy of IFN and ribavirin; (2) the recurrence of hepatitis C was lower in the group treated with the adjuvant agent than the placebo group; (3) in the group treated with adjuvant agent, the patients who exhibited an SVR remained HCV-free for one year after the treatment was completed; and (4) ribavirin did not appear to improve the therapeutic effect for hepatitis C in this study.

3. Clinical Trial #3

A total 32 patients infected with hepatitis C were treated with interferon-α 2A (ROFERON-A, Roche, "IFN") at 3

MU, three times a week subcutaneously and ribavirin (COPEGUS, Roche, "ribavirin") at 1000 mg, twice a week for 6 months. All patients recruited in this study had not been previously treated with ROFERON-A or COPEGUS. On the second week, the patients were randomly assigned into two groups and either treated with the adjuvant agent of the invention at 3180 mg (about 70% to 80% (w/w) of *Hirsutella sinensis* mycelia, about 10% to 20% (w/w) of *Astragalus membranaceus* extract, and about 5% to 10% of zinc) per day (N=16) or placebo (N=16, adjuvant agent in which the active raw materials were replaced with microcrystalline cellulose) concurrently with ROFERON-A and COPEGUS until the treatment was completed. The patients were examined again in follow-up visits at 6 and 12 months.

Serum samples from each patient were analyzed for the presence of HCV RNA as discussed above. Table 12 summarizes the results for these patients. "Recurrence" is defined as patients who exhibited undetectable levels of HCV RNA at the end of conventional treatment but exhibited detectable levels of HCV RNA at 6 months post conventional treatment ("response" is defined as the percentage of patients who showed no detectable levels of HCV RNA).

TABLE 12

Patients showing no detectable levels of HCV RNA after treatment with IFN and ribavirin with adjuvant agent of the invention or placebo

| | Response | | | |
|---|---|---|---|---|
| Group | 3 Months | 6 Months | 6 Months Post Treatment | Recurrence |
| IFN + ribavirin + adjuvant | 16/16 (100%) | 16/16 (100%) | 15/16 (64%)* | 1/16 (6%) |
| IFN + ribavirin + placebo | 10/16 (63%) | 10/16 (63%) | 3/16 (19%)* | 7/16 (44%) |

*SVR

Table 13 summarizes the adverse events observed for these patients. The percentages indicate the number of patients who experienced a particular adverse event during the treatment period.

TABLE 13

Patients experiencing an adverse event during treatment with INF and ribavirin with adjuvant agent of the invention or placebo

| Adverse Event | INF + Ribavirin + Adjuvant | INF + Ribavirin + Placebo |
|---|---|---|
| Fever, headache, myalgia | 83% | 90% |
| Fatigue | 75% | 75% |
| Arthralgia | 83% | 75% |
| Irregular bowel movement | 63% | 83% |
| Mild hair loss | 56% | 63% |
| Rash | 69% | 69% |
| Depression | 63% | 69% |
| Irritability | 13% | 19% |
| Insomnia | 75% | 83% |
| Weight loss | 56% | 90% |
| Anemia | | |
| 10 g/dl < hemoglobin < 11 g/dl | 31% | 56% |
| 9 g/dl < hemoglobin < 10 g/dl | 6% | 13% |
| Hemoglobin < 9 g/dl | 6% | 0% |
| Leukopenia | | |
| 3,000/UL < leukocytes < 3,500/UL | 19% | 31% |
| 2,500/UL < leukocytes, 3,000/UL | 0% | 0% |
| Leukocytes < 2,500/UL | 19% | 6% |

Taken together, these results show that: (1) the combination therapy of interferon, ribavirin, and the adjuvant agent increased the sustained virological response rate and decreased the rate of relapse of hepatitis C; and (2) the adjuvant agent decreased several of the adverse events caused by conventional treatment with interferon and ribavirin, such as irregular bowel movement, weight loss, anemia and leukopenia.

E. Hepatitis C Clinical Trials 4 and 5

Two open label clinical trials were conducted to examine the effects of the adjuvant agent of the invention comprising *Paecilomyces hepiali* mycelia and *Astragalus membranaceus* extract for treating hepatitis C patients. For trial 4, patients were treated with interferon α-2a with ribavirin and the adjuvant agent described above for 24 weeks, and then with the adjuvant agent without α-interferon and ribavirin for another 24 weeks. For trial 5, the patients were assigned into two groups. The two groups were treated with or without (control group) the adjuvant agent of the invention concurrently with peginterferon α-2a and ribavirin for 24 weeks, and then with or without (control group) the adjuvant agent without α-interferon and ribavirin for another 24 weeks. Blood samples were collected and any side effects were documented throughout the experiment period. The dependent variables examined were: (1) blood chemistry: WBC, hemoglobin, platelet, BUN, creatinine, SGOT/SGPT, and HCV-RNA; and (2) occurrence of side effects.

1. Clinical Trial #4

A total 32 patients infected with hepatitis C were treated with interferon-α2A (ROFERON-A, Roche, "IFN") at 3 MU, three times a week subcutaneously and ribavirin (COPEGUS, Roche, "ribavirin") at 1000 (if body weight was <75 kg) or 1200 mg (if body weight was ≥75 kg) daily. All patients recruited in this study had not been previously treated with ROFERON-A or COPEGUS. The patients were infected with HCV genotype 1b (N=24) or HCV genotype 2a+2b (N=8). The patients were treated with the adjuvant agent of the invention at 3180 mg (about 70% to 80% (w/w) of *Paecilomyces hepiali* mycelia, about 10% to 20% (w/w) of *Astragalus membranaceus* extract, and about 5% to 10% of zinc) per day concurrently with ROFE RON-A and COPEGUS for 24 weeks (3 months), and then with the adjuvant agent without ROFERON-A and COPEGUS for another 24 weeks (6 months) until the treatment was completed. The patients were examined again in a follow-up visit at 6 months ("6 months post INF treatment").

Serum samples from each patient were analyzed for the presence of HCV RNA as discussed above. Table 14 summarizes the results for these patients ("response" is defined as the percentage of patients who showed no detectable levels of HCV RNA).

TABLE 14

Patients showing no detectable levels of HCV RNA after treatment with IFN and ribavirin and adjuvant agent of the invention

| | Response | | |
|---|---|---|---|
| HCV Genotype | 3 Months | 6 Months | 6 Months Post INF Treatment |
| 1b | 21/24 (87.5%) | 19/24 (79.2%) | 12/24 (50%)* |
| 2a + 2b | 8/8 (100%) | 8/8 (100%) | 7/8 (87.5%)* |

*SVR

Table 15 summarizes the undesirable effects for these patients. The percentages indicate the number of patients that experienced a particular adverse event during the first and sixth months of treatment.

TABLE 15

Patients experiencing an adverse event during treatment with INF
and ribavirin and adjuvant agent of the invention or placebo

| Effect | 1st Month | 6th Month |
|---|---|---|
| Fever | 97% | 0% |
| Fatigue | 94% | 72% |
| Rigors | 60% | 0% |
| Nausea, Vomiting | 9% | 3% |
| Myalgia | 81% | 34% |
| Asthenia | 59% | 0% |

Table 16 compares the anemia and leucopenia side effects for these patients to those listed in the REBETOL package insert for treatment with REBETOL and interferon α without the adjuvant composition of the invention. The percentages indicate the number of patients that experienced a particular adverse event during the treatment period.

TABLE 16

Patients experiencing anemia or leucopenia adverse events after
treatment with IFN and ribavirin and the adjuvant agent of
the invention

| Effect | REBETOL Package Insert | Clinical Trial Patients |
|---|---|---|
| Hemoglobin concentration <10 mg/dl | 14% | 9.4% |
| WBC | | |
| WHO grade 3 (1000-1999 cells/μl) | 21% | 0% |
| WHO grade 4 (<1000 cells/μl) | 7% | 0% |

These results show: (1) the combination therapy of interferon, ribavirin, and the adjuvant agent increased the sustained virological response rate for hepatitis C genotypes 1b and 2a+2b compared to published trial results of 36% for genotype 1b and 59% for genotype 2a+2b over a treatment period of 48 weeks, from Roche's package insert of ROFERON-A; and (2) the adjuvant agent exhibits a trend towards reducing some of the side effects caused by conventional treatment comprising interferon and ribavirin.

2. Clinical Trial #5

A total 37 patients infected with hepatitis C were treated with pegylated interferon-α 2A (PEGASUS, Roche, "Peg-IFN") at 180 mcg, once per week subcutaneously and ribavirin (COPEGUS, Roche, "ribavirin") at 1000 (if body weight was <75 kg) or 1200 mg (if body weight was ≥75 kg) daily. All patients recruited in this study had not been previously treated with PEGASUS or COPEGUS. The patients were assigned into two groups. The two groups were treated with or without the adjuvant agent of the invention at 3180 mg (about 70% to 80% (w/w) of Paecilomyces hepiali mycelia, about 10% to 20% (w/w) of Astragalus membranaceus extract, and about 5% to 10% of zinc) per day concurrently with PEGASUS and COPEGUS for 24 weeks, and then with (N=20) or without (N=17) the adjuvant agent without PEGASUS or COPEGUS for another 24 weeks.

Figure 2:
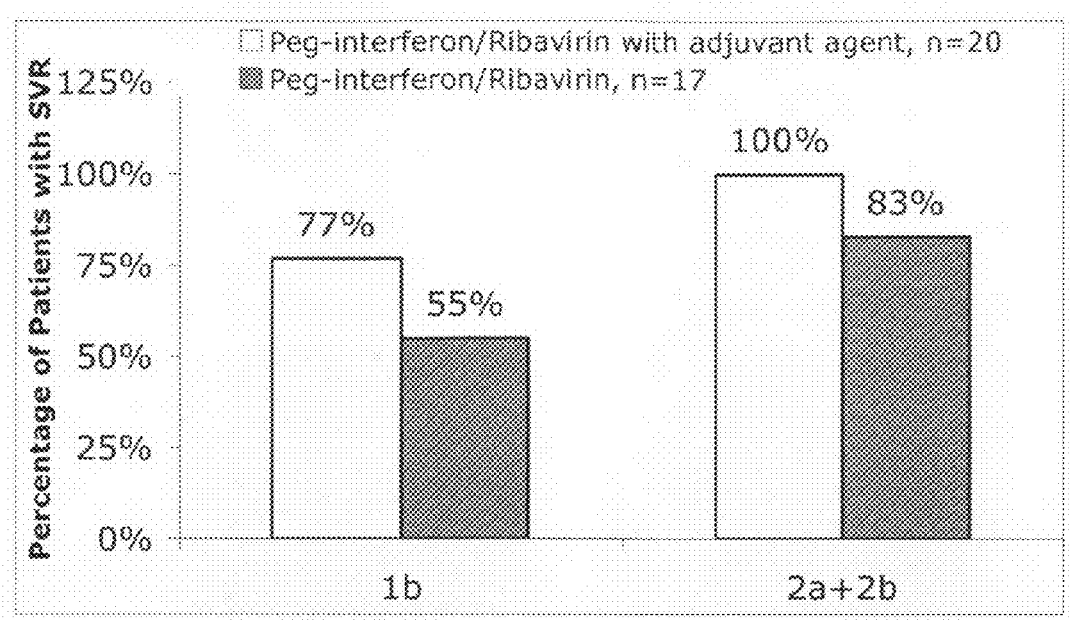
FIG. 2. Results from treating patients infected with HCV genotype 1b or 2a and 2b with pegylated-interferon-α at 180 mcg/vial weekly for 24 weeks in combination with ribavirin at 1000 (if body weight was <75 kg) or 1200 mg (if body weight was ≥75 kg) daily for 24 weeks, with or without adjuvant agent comprising *Paecilomyces hepiali* mycelia and *Astragalus membranaceus* extract. The data are presented as the percentage of patients showing a sustained virus response (SVR), defined as undetectable HCV RNA virus at 6 months after the end of conventional treatment with interferon and ribavirin.

FIG. 2 summarizes the response rates for these patients. The figure shows the SVR for in patients infected with HCV genotypes 1b and 2a+2b with and without adjuvant.

These results show that the combination therapy of peg-interferon α-2a, ribavirin, and the adjuvant agent of the invention increased the sustained virological response rate for hepatitis C genotype 1b by 22% (from 55% to 77%) and by 17% (from 83% to 100%) for genotypes 2a+2b compared to peg-interferon and ribavirin alone.

F. Hepatitis B Experiment

The hepatitis B virus producing cell lines, 1.3ES8 and HepG2.2.15, which express the adw and ayw genotypes of Hepatitis B, respectively, were used to evaluate the effect of the mycelia of the invention on the levels of HBs and HBe surface antigens. The 1.3ES8 and HepG2.2.15 cell lines are human hepatoma cells that have been stably transfected with the HBV genome (see Journal of Virology, 2005 February; 79(3): 1813-1823, and Journal of Virology, 2003 May; 77(9): 5503-5506). These cells produce infectious HBV viral particles and secrete the HBV HBs and HBe antigens into the culture medium.

The 1.3ES8 and HepG2.2.15 cells were cultured for two and four days (day 2 and day 4), respectively, with or without the adjuvant agent of the invention (200 μg/ml in DMSO) (about 70% to 80% (w/w) of Paecilomyces hepiali mycelia, about 10% to 20% (w/w) of Astragalus membranaceus extract, and about 5% to 10% of zinc). The culture medium was collected and stored at −20° C. for testing. 50 μl of the cell culture media was added to ELISA plates coated with anti-HBs or anti-HBe and analyzed according to manufacturer's instructions (SURASE B-96 (TMB) (GENERAL BIOLOGICALS, 4SGE3) was used for HBs measurement, and EASE BN-96 (TMB) (GENERAL BIOLOGICALS, 4BNE3) was for HBe measurement). Briefly, the plates were incubated at 40° C. for 2 hours for the HBs test, or at 40° C. overnight for HBe test. The wells were washed six times with washing buffer and peroxidase conjugated antibody was added. 50 μl of anti-HBs-peroxidase and 100 μl of anti-HBe-peroxidase was added, respectively. After a 1 hour incubation at 40° C., the wells were washed six times with washing buffer. 100 μl of tetramethylbenzidine (TMB) substrate was added and the plates were incubated in the dark for 30 minutes. Finally, 100 μl of 2M $H_2SO_4$ was added to stop the reaction. The absorbance was read at a wavelength of 450 nm in an ELISA plate reader.

Table 17 summarizes the results of these experiments. "Inhibition rate" refers to the ability of the adjuvant agent of the invention to inhibit the secretion of HBs and HBe antigen by the 1.3ES8 and HepG2.2.15 cells (percentages indicate the amount of inhibition relative to control cells that were not treated with the adjuvant agent of the invention).

TABLE 17

Relative level of inhibition of HBV surface antigen expression in
cells treated with adjuvant agent of the invention

| | Inhibition Rate | | | |
|---|---|---|---|---|
| | Day 2 | | Day 4 | |
| | 1.3ES8 Cells | HepG2.2.15 Cells | 1.3ES8 Cells | HepG2.2.15 Cells |
| HBs antigen | 22% | 7% | 22% | 20% |
| HBe antigen | 62% | 0% | 62% | 26% |

These results show that the adjuvant agent of the invention inhibits secretion of hepatitis B HBs and HBe antigens. The results also show that the adjuvant agent has greater inhibitory effects in 1.3ES8 cells than in HepG2.2.15 cells. Thus, the data demonstrate that the adjuvant agent of the invention has a greater anti-viral effect on the adw genotype of hepatitis B than the ayw genotype.

Based on the in vitro, in vivo, and human studies described above, it is clear that Cordyceps sinensis fermentation products have a number of beneficial therapeutic uses. The bioassay studies revealed that *Cordyceps sinensis* fermentation products produced by the method of the invention show much higher potency for immune-stimulation than mycelia from other sources. In addition, potency can be enhanced by adding *Astragalus membranaceus* extracts to the *Cordyceps sinensis* fermentation products. The bioassay studies also indicate that the adjuvant agents of the invention comprising *Cordyceps sinensis* fermentation products have a strong ability to kill hepatitis C virus in human liver cells in vitro. The human studies confirm these in vitro and in vivo results by demonstrating that the adjuvant agent of the invention not only increases the cure rate of HCV patients treated with conventional treatment, but also decreases the adverse effects caused by conventional treatments. Thus, the adjuvant agents of the invention have novel and non-obvious therapeutic utility.

The invention claimed is:

1. A method for producing *Cordyceps sinensis* fermentation product comprising:
   (a) inoculating a plate culture comprising solid nutrient medium with at least one strain of *Cordyceps sinensis* and incubating the inoculated plate culture at about 18° C. to about 28° C. for about 4 to 8 days;
   (b) inoculating a first seed culture comprising liquid nutrient medium with at least a portion of the inoculated plate culture from step (a) and incubating the first seed culture at about 18° C. to about 28° C. for about 2 to 4 days;
   (c) inoculating a second seed culture comprising liquid nutrient medium with at least a portion of the inoculated plate culture from step (b) and incubating the second seed culture at about 18° C. to about 28° C. for about 2 to 3 days;
   (d) inoculating a fermentation culture comprising liquid nutrient medium with a least a portion of the incubated seed culture from step (c) and incubating the fermentation culture at about 18° C. to about 28° C. for about 1 to 3 days; and
   (e) recovering the *Cordyceps sinensis* fermentation product from the incubated fermentation culture of step (d), wherein the nutrient media in steps (a) through (d) each comprise: about 0.001% to about 0.01% (w/w) copper and about 0.0003% to about 0.003% (w/w) selenium.

2. A pharmaceutical composition comprising a *Cordyceps sinensis* fermentation product produced by a method comprising:
   (a) inoculating a plate culture comprising solid nutrient medium with at least one strain of *Cordyceps sinensis* and incubating the inoculated plate culture at about 18° C. to about 28° C. for about 4 to 8 days;
   (b) inoculating a first seed culture comprising liquid nutrient medium with at least a portion of the inoculated plate culture from step (a) and incubating the first seed culture at about 18° C. to about 28° C. for about 2 to 4 days;
   (c) inoculating a second seed culture comprising liquid nutrient medium with at least a portion of the inoculated plate culture from step (b) and incubating the second seed culture at about 18° C. to about 28° C. for about 2 to 3 days;
   (d) inoculating a fermentation culture comprising liquid nutrient medium with a least a portion of the incubated seed culture from step (c) and incubating the fermentation culture at about 18° C. to about 28° C. for about 1 to 3 days; and
   (e) recovering the *Cordyceps sinensis* fermentation product from the incubated fermentation culture of step (d), wherein the nutrient media in steps (a) through (d) each comprise: about 0.001% to about 0.01% (w/w) copper and about 0.0003% to about 0.003% (w/w) selenium; and a pharmaceutically acceptable carrier.

3. A method for treating a patient infected with or exposed to hepatitis C comprising administering effective amounts of:
   the composition of claim 2;
   an interferon; and
   a guanosine analog;
   to a patient in need thereof.

4. The method of claim 3, further comprising administering an effective amount of an extract from *Astragalus membranaceus*.

5. A method for treating a patient infected with or exposed to hepatitis B, comprising administering a therapeutically effective amount of the composition of claim 2 to a patient in need thereof.

6. A method for producing *Cordyceps sinensis* fermentation product comprising:
   (a) inoculating a plate culture comprising solid nutrient medium with at least one strain of *Cordyceps sinensis* and incubating the inoculated plate culture at about 18° C. to about 28° C. for about 4 to 8 days;
   (b) inoculating a first seed culture comprising liquid nutrient medium with at least a portion of the inoculated plate culture from step (a) and incubating the first seed culture at about 18° C. to about 28° C. for about 2 to 4 days;
   (c) inoculating a second seed culture comprising liquid nutrient medium with at least a portion of the inoculated plate culture from step (b) and incubating the second seed culture at about 18° C. to about 28° C. for about 2 to 3 days;
   (d) inoculating a fermentation culture comprising liquid nutrient medium with a least a portion of the incubated seed culture from step (c) and incubating the fermentation culture at about 18° C. to about 28° C. for about 3 to 7 days; and
   (e) recovering the *Cordyceps sinensis* fermentation product from the incubated fermentation culture of step (d), wherein the method does not comprise additional culture steps between steps (a) and (b), (b) and (c), and/or (c) and (d), and wherein the nutrient media in steps (a) through (d) each comprise: about 0.001% to about 0.01% (w/w) copper and about 0.0003% to about 0.003% (w/w) selenium.

7. A pharmaceutical composition comprising a *Cordyceps sinensis* fermentation product produced by a method comprising:
   (a) inoculating a plate culture comprising solid nutrient medium with at least one strain of *Cordyceps sinensis* and incubating the inoculated plate culture at about 18° C. to about 28° C. for about 4 to 8 days;
   (b) inoculating a first seed culture comprising liquid nutrient medium with at least a portion of the inoculated plate culture from step (a) and incubating the first seed culture at about 18° C. to about 28° C. for about 2 to 4 days;
   (c) inoculating a second seed culture comprising liquid nutrient medium with at least a portion of the inoculated plate culture from step (b) and incubating the second seed culture at about 18° C. to about 28° C. for about 2 to 3 days;
   (d) inoculating a fermentation culture comprising liquid nutrient medium with a least a portion of the incubated seed culture from step (c) and incubating the fermentation culture at about 18° C. to about 28° C. for about 3 to 7 days; and
   (e) recovering the *Cordyceps sinensis* fermentation product from the incubated fermentation culture of step (d), wherein the method does not comprise additional culture steps between steps (a) and (b), (b) and (c), and/or (c) and (d), and wherein the nutrient media in steps (a) through (d) each comprise: about 0.001% to about 0.01% (w/w) copper and about 0.0003% to about 0.003% (w/w) selenium; and a pharmaceutically acceptable carrier.

8. A method for treating a patient infected with or exposed to hepatitis C comprising administering effective amounts of:
the composition of claim 7;
an interferon; and
a guanosine analog;
to a patient in need thereof.

9. The method of claim 8, further comprising administering an effective amount of an extract from *Astragalus membranaceus*.

10. A method for treating a patient infected with or exposed to hepatitis B, comprising administering a therapeutically effective amount of the composition of claim 7 to a patient in need thereof.

11. An adjuvant composition for use with a conventional therapy for treating a patient infected with or exposed to hepatitis C comprising:
about 50% to about 90% (w/w) of a *Cordyceps sinensis* fermentation product; and about 10% to about 50% (w/w) of an *Astragalus membranaceus* extract; and
a pharmaceutically acceptable carrier,
wherein the adjuvant composition enhances the sustained virological response of the convention therapy, and wherein the *Cordyceps sinensis* fermentation product is produced by a method comprising:
(a) inoculating a plate culture comprising solid nutrient medium with at least one strain of *Cordyceps sinensis* and incubating the inoculated plate culture at about 18° C. to about 28° C. for about 4 to 8 days;
(b) inoculating a first seed culture comprising liquid nutrient medium with at least a portion of the inoculated plate culture from step (a) and incubating the first seed culture at about 18° C. to about 28° C. for about 2 to 4 days;
(c) inoculating a second seed culture comprising liquid nutrient medium with at least a portion of the inoculated plate culture from step (b) and incubating the second seed culture at about 18° C. to about 28° C. for about 2 to 3 days;
(d) inoculating a fermentation culture comprising liquid nutrient medium with a least a portion of the incubated seed culture from step (c) and incubating the fermentation culture at about 18° C. to about 28° C. for about 1 to 3 days; and (e) recovering the *Cordyceps sinensis* fermentation product from the incubated fermentation culture of step (d), wherein the nutrient media in steps (a) through (d) each comprise: about 0.001% to about 0.01% (w/w) copper and about 0.0003% to about 0.003% (w/w) selenium.

12. The composition of claim 11, wherein the *Cordyceps sinensis* is *Paecilomyces hepiali*.

13. The composition of claim 11, further comprising zinc.

14. The composition of claim 13, wherein the concentration of *Cordyceps sinensis* fermentation product is about 70% to about 80% (w/w), the concentration of *Astragalus membranaceus* extract is about 10% to about 20% (w/w), and the concentration of zinc is about 5% to about 10%.

15. A method for treating a patient infected with or exposed to hepatitis C comprising administering effective amounts of:
the composition of claim 11;
an interferon; and
a guanosine analog;
to a patient in need thereof.

16. The method of claim 15, wherein the interferon is a pegylated interferon-α 2A and the guanosine is ribavirin.

17. The method of claim 15, wherein the composition of claim 11, the interferon, and the ribavirin are administered simultaneously.

18. The method of claim 15, wherein the composition of claim 11, the interferon, and the ribavirin are administered sequentially.

19. The pharmaceutical composition of claim 2, wherein the nutrient media in steps (a) through (d) each further comprise: about 0.01% to about 0.2% (w/w) manganese and/or about 0.01% to about 0.2% (w/w) iron and/or about 0.02% to about 0.2% (w/w) cobalt and/or about 0.05% to about 0.5% (w/w) calcium and/or zinc.

20. The pharmaceutical composition of claim 7, wherein the nutrient media in steps (a) through (d) each further comprise: about 0.01% to about 0.2% (w/w) manganese and/or about 0.01% to about 0.2% (w/w) iron and/or about 0.02% to about 0.2% (w/w) cobalt and/or about 0.05% to about 0.5% (w/w) calcium and/or zinc.

21. The adjuvant composition of claim 11, wherein the nutrient media in steps (a) through (d) each further comprise: about 0.01% to about 0.2% (w/w) manganese and/or about 0.01% to about 0.2% (w/w) iron about 0.02% to about 0.2% (w/w) cobalt and/or about 0.05% to about 0.5% (w/w) calcium and/or zinc.

* * * * *